United States Patent
Sweat et al.

(10) Patent No.: US 8,066,888 B2
(45) Date of Patent: Nov. 29, 2011

(54) BLOOD PROCESSING APPARATUS WITH CONTROLLED CELL CAPTURE CHAMBER TRIGGER

(75) Inventors: William Sweat, Lakewood, CO (US); Jeremy Kolenbrander, Brighton, CO (US); John R. Lindner, Morrison, CO (US); Jennifer Hinz, Thornton, CO (US)

(73) Assignee: CaridianBCT, Inc., Lakewood, CO (US)

( * ) Notice: Subject to any disclaimer, the term of this patent is extended or adjusted under 35 U.S.C. 154(b) by 733 days.

(21) Appl. No.: 12/238,697

(22) Filed: Sep. 26, 2008

(65) Prior Publication Data

US 2009/0166297 A1 Jul. 2, 2009

Related U.S. Application Data

(60) Provisional application No. 61/017,045, filed on Dec. 27, 2007.

(51) Int. Cl.
*B01D 21/32* (2006.01)
(52) U.S. Cl. .............. 210/745; 210/787; 210/87; 494/2; 494/7; 494/20; 494/37
(58) Field of Classification Search .................. 210/745, 210/787, 87; 494/2, 7, 20, 37
See application file for complete search history.

(56) References Cited

U.S. PATENT DOCUMENTS

| | | | |
|---|---|---|---|
| 4,094,461 A | 6/1978 | Kellogg et al. | |
| 4,151,844 A | 5/1979 | Cullis et al. | |
| 4,425,112 A | 1/1984 | Ito | |
| 4,493,691 A | 1/1985 | Calari | |
| 4,557,719 A | 12/1985 | Neumann et al. | |
| 4,567,373 A | 1/1986 | O'Meara et al. | |
| 4,647,279 A | 3/1987 | Mulzet et al. | |
| 4,670,002 A | 6/1987 | Brown et al. | |
| 4,671,102 A | 6/1987 | Vinegar et al. | |
| 4,724,317 A | 2/1988 | Brown et al. | |

(Continued)

FOREIGN PATENT DOCUMENTS

EP 0392475 10/1990

(Continued)

OTHER PUBLICATIONS

International Search Report for PCT/US2008/077924, filed Sep. 26, 2008; mailed Jan. 19, 2009.

(Continued)

*Primary Examiner* — David A Reifsnyder
(74) *Attorney, Agent, or Firm* — John R. Merkling; Edna M. O'Connor; Laura B. Arciniegas

(57) ABSTRACT

A blood cell collection system having means for detecting when a cell separation chamber has filled with white blood cells, and flushing the cells out of the cell separation chamber into a collect bag. A red-green sensor senses the optical characteristics of fluid leaving the cell separation chamber. A baseline value is calculated. The device calculates a ratio of the intensities of red light and green light and a peak-to-peak ratio of intensities. If either ratio exceeds thresholds computed from the baseline, the device flushes the cells into the collect bag. A camera detects white cells passing into the cell separation chamber and the device calculates the number of cells being collected. If the calculated number of collected cells exceeds a certain limit, the cell separation chamber is flushed. If the device is unable to establish a baseline, the donation can proceed, relying solely on the calculated number of collected cells.

32 Claims, 17 Drawing Sheets

U.S. PATENT DOCUMENTS

| | | | |
|---|---|---|---|
| 4,834,890 A | 5/1989 | Brown et al. |
| 5,076,911 A | 12/1991 | Brown et al. |
| 5,104,526 A | 4/1992 | Brown et al. |
| 5,260,598 A | 11/1993 | Brass et al. |
| 5,316,667 A | 5/1994 | Brown et al. |
| 5,322,620 A | 6/1994 | Brown et al. |
| 5,653,887 A | 8/1997 | Wahl et al. |
| 5,722,926 A | 3/1998 | Hlavinka et al. |
| 5,734,464 A | 3/1998 | Gibbs |
| 5,814,279 A | 9/1998 | Biesel et al. |
| 5,889,584 A | 3/1999 | Wardlaw |
| 5,930,033 A | 7/1999 | Inove et al. |
| 5,936,714 A | 8/1999 | Gibbs |
| 5,948,271 A | 9/1999 | Wardwell et al. |
| 5,951,877 A | 9/1999 | Langley et al. |
| 6,006,119 A | 12/1999 | Soller et al. |
| 6,053,856 A | 4/2000 | Hlavinka |
| 6,071,422 A | 6/2000 | Hlavinka et al. |
| 6,254,784 B1 | 7/2001 | Nyak et al. |
| 6,334,842 B1 | 1/2002 | Hlavinka et al. |
| 6,338,820 B1 | 1/2002 | Hubbard et al. |
| 6,354,986 B1 | 3/2002 | Hlavinka et al. |
| 6,506,606 B1 | 1/2003 | Winkelman et al. |
| 6,514,189 B1 | 2/2003 | Hlavinka et al. |
| 6,632,399 B1 | 10/2003 | Kellogg et al. |
| 6,790,371 B2 | 9/2004 | Dolecek |
| 7,327,443 B2 | 2/2008 | Scibona et al. |
| 7,422,693 B2 | 9/2008 | Carter et al. |
| 2002/0147094 A1 | 10/2002 | Dolecek |
| 2002/0196435 A1 | 12/2002 | Cohen et al. |
| 2003/0113930 A1 | 6/2003 | Winkelman et al. |
| 2007/0102374 A1 | 5/2007 | Kolenbrander |

FOREIGN PATENT DOCUMENTS

| | | |
|---|---|---|
| EP | 0729790 | 1/1996 |
| EP | 1 749 546 | 2/2007 |
| JP | 04371245 | 12/1992 |
| WO | WO01/18396 | 3/2001 |

OTHER PUBLICATIONS

Salgaller, Michael L. "A Manifesto on the Current State of Dendritic Cells in Adoptive Immunotherapy", *Transfusion*, 2003, 43(4):422-424.

BLOOD PROCESSING APPARATUS WITH CONTROLLED CELL CAPTURE CHAMBER TRIGGER

This application claims priority of U.S. Provisional application Ser. No. 61/017,045 filed Dec. 27, 2007. This application is related to U.S. patent application Ser. No. 11/163,969, filed Nov. 4, 2005, published on May 10, 2007 as Pub. No. 2007/0102374A1, and now abandoned. Further related patents include U.S. Pat. No. 5,722,926, issued Mar. 3, 1998; U.S. Pat. No. 5,951,877, issued Sep. 14, 1999; U.S. Pat. No. 6,053,856, issued Apr. 25, 2000; U.S. Pat. No. 6,334,842, issued Jan. 1, 2002; U.S. Pat. No. 7,422,693 B2, issued Sep. 9, 2008; and U.S. Pat. No. 7,327,443 B2, issued Feb. 5, 2008. The entire disclosures of the provisional patent application, the patent publication and all of the U.S. patents are incorporated herein by reference.

FIELD OF THE INVENTION

The present invention relates to an apparatus and method for separating particles or components of a fluid. The invention has particular advantages in connection with separating blood components, such as white blood cells and platelets.

DESCRIPTION OF THE RELATED ART

In many different fields, liquids carrying particles must be filtered or processed to obtain either a purified liquid or purified particle end product. In its broadest sense, a filter is any device capable of removing or separating particles from a substance. Thus, the term "filter" as used herein is not limited to a porous media material but includes many different types of devices and processes where particles are either separated from one another or from liquid.

In the medical field, it is often necessary to filter blood. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets. Most current purification devices rely on density and size differences or surface chemistry characteristics to separate and/or filter the blood components.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating at a very rapid speed and centrifugal force stratifies the blood components, so that particular components may be separately removed. Components are removed through ports arranged within stratified layers of blood components.

White blood cells and platelets in plasma form a medium-density, stratified layer or "buffy coat". Because typical centrifuge collection processes are unable to consistently and satisfactorily separate white blood cells from platelets in the buffy coat, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5-20% of the platelets. These conventional filters may also reduce "platelet viability", meaning that once the platelets pass through a filter, a percentage of the platelets cease to function properly and may be partially or fully activated. In addition, porous filters may cause the release of bradykinin, an inflammation mediator and vasodialator, which may lead to hypotensive episodes in a patient. Porous filters are also expensive and often require additional time-consuming manual labor to perform a filtration process. Although porous filters are effective in removing a substantial number of white blood cells, activated platelets may clog the filter. Therefore, the use of at least some porous filters is not feasible in on-line processes.

Another separation process is one known as centrifugal elutriation. This process separates cells suspended in a liquid medium without the use of a membrane filter. In one common form of elutriation, a cell batch is introduced into a flow of liquid elutriation buffer. This liquid, which carries the cell batch in suspension, is then introduced into a funnel-shaped chamber located on a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal processing separates particles having different sedimentation velocities. Stoke's law describes sedimentation velocity ($V_S$) of a spherical particle as follows:

$$V_S = (((D^2_{cell} * (\rho_{cell} - \rho_{medium}))/(18 * \mu_{medium})) * \omega^2 r$$

Where D is the diameter of the cell or particle, $\rho_{cell}$ is the density of the particle, $\rho_{medium}$ is the density of the liquid medium, $\mu_{medium}$ is the viscosity of the medium, and $\omega$ is the angular velocity and r is the distance from the center of rotation to the cell or particle. Because the diameter of a particle is raised to the second power in Stoke's equation and the density of the particle is not, the size of a cell, rather than its density, greatly influences its sedimentation rate. This explains why larger particles generally remain in a chamber during centrifugal processing, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate, discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

For these and other reasons, there is a need to improve particle separation and/or separation of components of a fluid.

SUMMARY OF THE INVENTION

The present invention comprises a centrifuge for separating particles suspended in a fluid, particularly blood and blood components, and methods for controlling the centrifuge. The apparatus has a blood processing vessel mounted on a rotor, the blood processing vessel having a fluid inlet and a fluid outlet, the fluid inlet being radially outward from the fluid outlet. The apparatus may further comprise at least one pump controlling a rate of fluid flow through the blood processing vessel, a camera configured to observe fluid flow with respect to the blood processing vessel, and a controller receiving signals from the camera and controlling the motor and the pump. A cell separation or elutriation chamber is connected to the fluid outlet of the blood processing vessel. Particles, such as white blood cells, are selectively captured in the cell separation chamber and flushed out of the cell separation chamber.

The present invention provides means for detecting when the cell separation chamber has filled with white blood cells, flushing the white blood cells out of the cell separation chamber into a collect bag, and resuming collection of white blood cells in the cell separation chamber. The red-green sensor senses the optical characteristics of the fluid leaving the cell separation chamber. The device calculates a baseline value characteristic of the particular donor. The device also calculates a red-green ratio of the intensities of red light and green light and a peak-to-peak ratio of intensities. If either the red-green ratio or the peak-to-peak ratio exceeds thresholds computed from the baseline value, the device increases flow through the cell separation chamber, causing the white blood cells to be flushed into the collect bag. In addition, the camera detects white cells passing into the cell separation chamber and the device calculates the number of cells being collected. If the calculated number of collected cells exceeds a certain limit, the cell separation chamber is flushed, even though neither the threshold of the red-green ratio nor the threshold of the peak-to-peak ratio has been exceeded. If the device is unable to establish a baseline, the donation can proceed, relying solely on the calculated number of collected cells. In addition to the red-green sensor in the outflow line of the cell separation chamber, a camera can detect blood components in an outflow line leading out of blood processing vessel and into the cell separation chamber. From the known volume of the chamber and a representative size of white blood cells, the device can estimate the quantity of white blood cells in the chamber. If the estimated quantity is too low when a trigger event from either the red-green ratio or the peak-to-peak ratio is detected, the trigger event may be disregarded. If the estimated quantity is too high before a trigger event is detected, the chamber may nevertheless be flushed. If the conditions were not stable enough to set a baseline, with associated thresholds, the chamber may be flushed at a selected estimated capacity.

If baseline values can be established, the device is able to fill the cell separation chamber with white blood cells and empty the cells into a collection bag efficiently, thereby improving the donation process. The red-green ratio and peak-to-peak criteria are sensitive indicators that the chamber has filled with white blood cells, thus allowing an efficient collection procedure. The algorithm also distinguishes between stable and unstable flow conditions and applies sensitive criteria when flow conditions are smooth and less sensitive criteria when flow disturbances are detected. The present invention allows for efficient collection of white blood cells from a single donor by monitoring the outflow characteristics of the cell collection chamber. Such efficient collection is believed to contribute to reduced donation times and higher quality white cell collections.

It is to be understood that both the foregoing general description and the following detailed description are exemplary, and are intended to provide further explanation of the invention as claimed.

DETAILED DESCRIPTION

To describe the present invention, reference will now be made to the accompanying drawings. The present invention comprises a blood processing apparatus having a camera control system, as disclosed in U.S. patent application Ser. No. 11/163,969, application Ser. No. 10/884,877 and application Ser. No. 10/905,353. It may also be practiced with a TRIMA® blood component centrifuge manufactured by Gambro BCT, Inc. of Colorado or, alternatively, with a COBE® SPECTRA™ single-stage blood component centrifuge also manufactured by Gambro BCT, Inc. Both the TRIMA® and the SPECTRA™ centrifuges incorporate a one-omega/two-omega sealless tubing connection as disclosed in U.S. Pat. No. 4,425,112 to Ito, the entire disclosure of which is incorporated herein by reference. The SPECTRA™ centrifuge also uses a single-stage blood component separation channel substantially as disclosed in U.S. Pat. No. 4,094,461 to Kellogg et al. and U.S. Pat. No. 4,647,279 to Mulzet et al., the entire disclosures of which are also incorporated herein by reference. The invention could also be practiced with a TRIMA® or TRIMA ACCEL® centrifugal separation system or other types of centrifugal separator. The method of the invention is described in connection with the aforementioned blood processing apparatus and camera control system for purposes of discussion only, and this is not intended to limit the invention in any sense.

Figure 1:
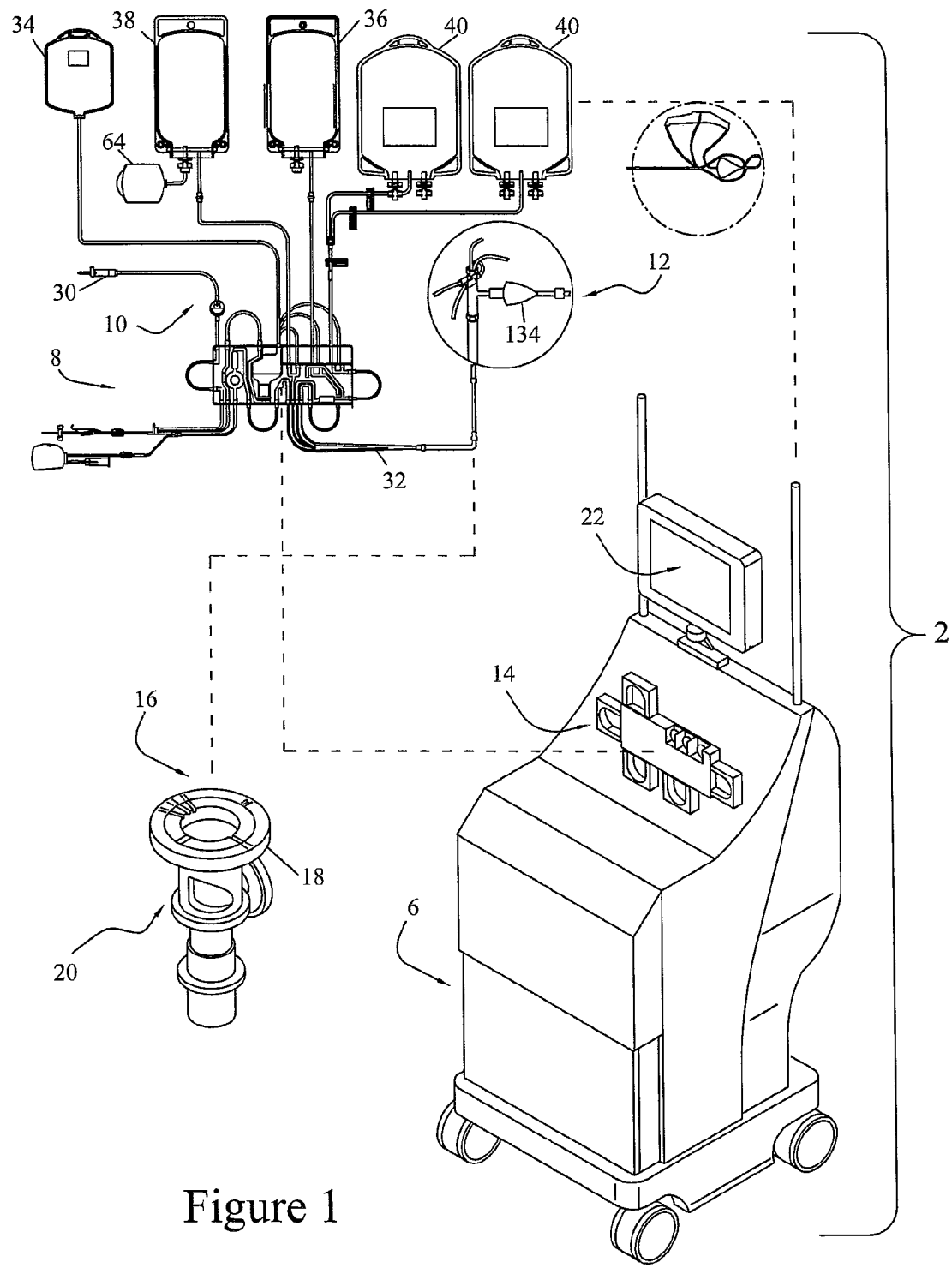
FIG. 1 is a schematic view of one embodiment of an apharesis system, which can be used in or with the present invention.

A preferred blood apharesis system 2 for use in and/or with the present invention is schematically illustrated in FIG. 1. System 2 provides for a continuous blood component separation process. Generally, whole blood is withdrawn from a donor and is substantially continuously provided to a blood component separation device 6 where the blood is continuously separated into various component types and at least one of these blood component types is continuously collected from the device 6. One or more of the separated blood components may then either be provided for collection and subsequent use by another through transfusion or may be uncollected and then returned to the donor. Therapeutic treatment and near immediate return of certain separated blood components is a viable, yet less common alternative use hereof as well. It is also understood that for therapeutic treatment the blood may be separated into components with filtration using the principles of the instant invention and as described below at a patient's bedside for return to such patient.

In the blood apharesis system 2, blood is withdrawn from the donor and directed through a pre-connected bag and tubing set 8, which includes an extracorporeal tubing circuit 10, and a disposable blood processing vessel 12, which together define a closed, sterile and disposable system. The set 8 is disposable and is adapted to be mounted on and/or in the blood component separation device 6. The separation device 6 includes a pump/valve/sensor assembly 14 for interfacing with the extracorporeal tubing circuit 10, and a centrifuge assembly 16 for interfacing with the blood processing vessel 12.

The centrifuge assembly 16 may include a channel 18 in a rotatable rotor assembly 20, which provides the centrifugal forces required to separate blood into its various blood component types by centrifugation. The blood processing vessel 12 may then be fitted within the channel 18. When thus connected as described, blood can then be flowed substantially continuously from the donor, through the extracorporeal tubing circuit 10, and into the rotating blood processing vessel 12. The blood within the blood processing vessel 12 may then be continuously separated into various blood component types and at least one of these blood component types (e.g., white blood cells, platelets, plasma, or red blood cells) is continually removed from the blood processing vessel 12. Blood components that are not being retained for collection or for therapeutic treatment (e.g., platelets and/or plasma) are also removed from the blood processing vessel 12 and returned to the donor via the extracorporeal tubing circuit 10. Various alternative apharesis systems (not shown) may also make use of the present invention, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 6 is controlled by one or more processors included therein, and may advantageously comprise a plurality of embedded computer processors to accommodate interface with ever-increasing PC user facilities (e.g., CD ROM, modem, audio, networking and other capabilities). In order to assist the operator of the apharesis system 2 with various aspects of its operation, the blood component separation device 6 includes a graphical interface 22 with an interactive touch screen.

Further details concerning the operation of a preferred apharesis system, such as the Gambro Trima® System and the Trima Accel® System (available from the assignee of this application, Gambro BCT, Inc., Lakewood, Colo.) may be found in a plurality of publications, including, for example, WO99/11305 and U.S. Pat. Nos. 5,653,887; 5,676,644; 5,702,357; 5,720,716; 5,722,946; 5,738,644; 5,750,025; 5,795,317; 5,837,150; 5,919,154; 5,921,950; 5,941,842; and 6,129,656; among numerous others. The disclosures hereof are incorporated herein as if fully set forth. A plurality of other known apharesis systems may also be useful herewith, as for example, the Baxter CS3000® and/or Amicus® and/or Auto-pheresis-C® and/or Alyx systems, and/or the Haemonetics MCS® or MCS®+ and/or the Fresenius COM.TEC™ or AS-104™ and/or like systems.

Disposable Set: Extracorporeal Tubing Circuit

Figure 2:
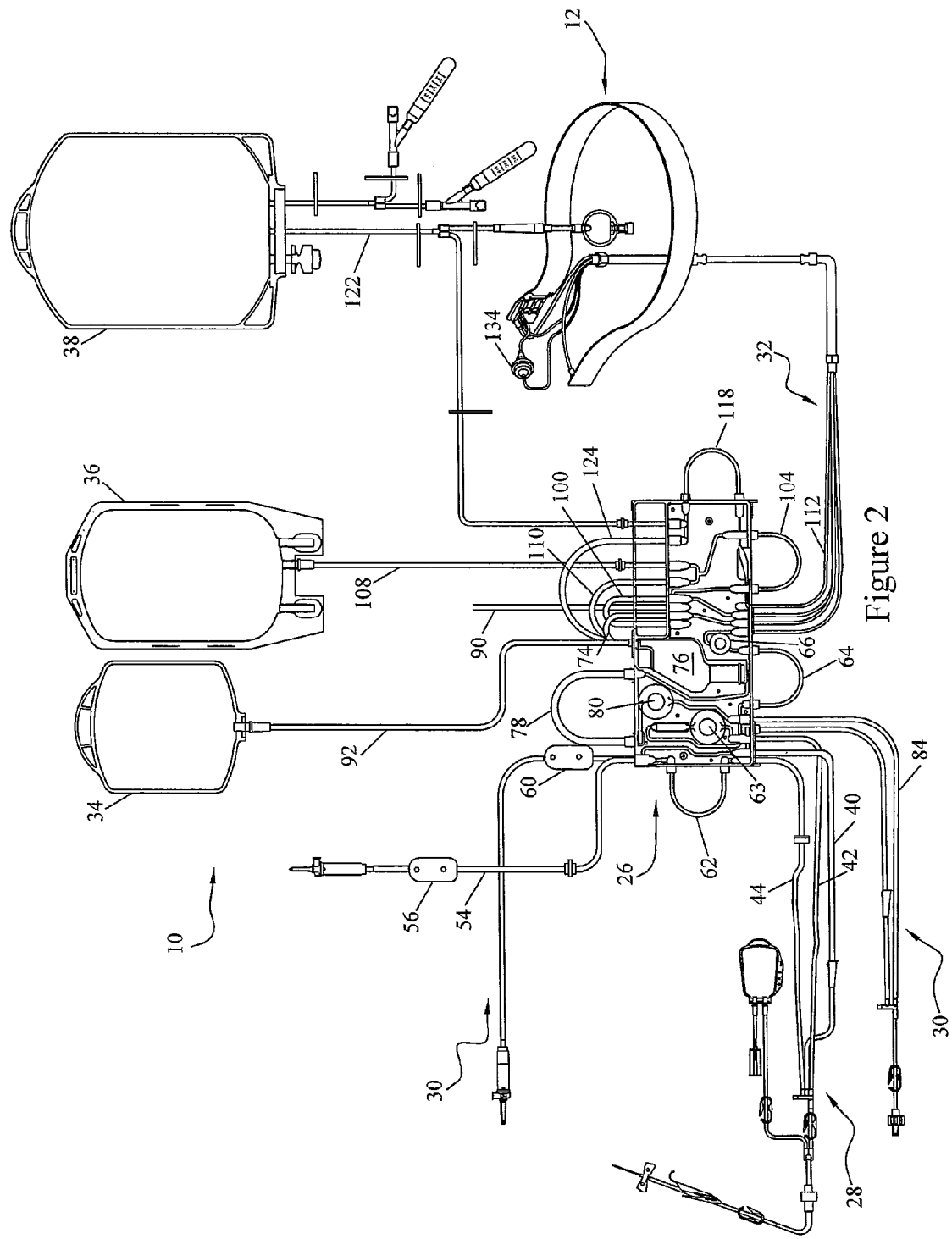
FIG. 2 illustrates a tubing and bag set including an extracorporeal tubing circuit, a cassette assembly, and collection bag assembly for use in or with the system of FIG. 1 pursuant to the present invention.
Figure 3:
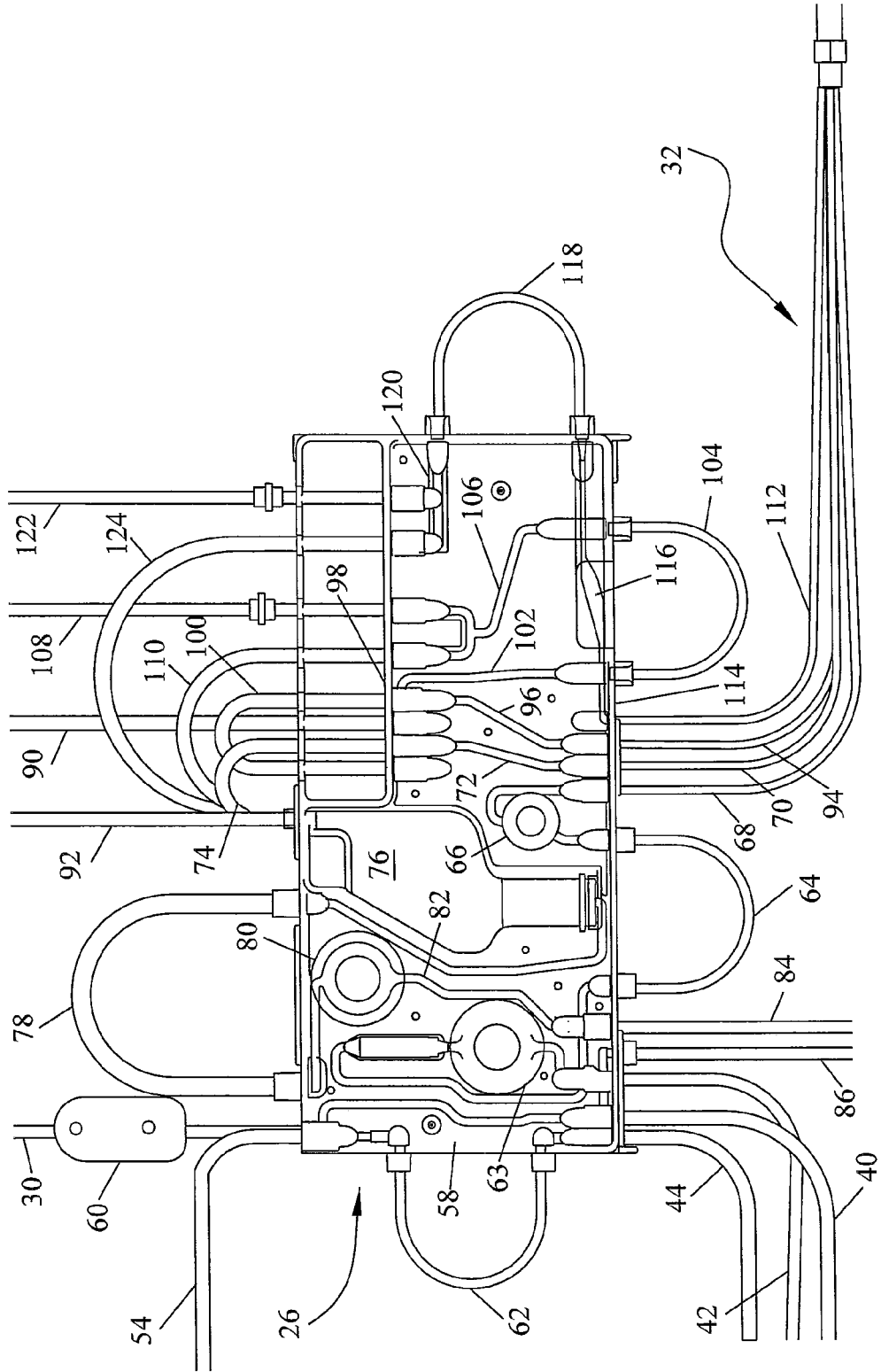
FIG. 3 illustrates a cassette assembly similar to that shown in the set of FIG. 2.

An extracorporeal tubing circuit 10 is shown in FIG. 2 and FIG. 3, which may include a cassette assembly 26 and a number of tubing/collection assemblies 28, 30, 32, 34, 36, 38 and 40. A blood removal tubing assembly 28 provides a needle interface for withdrawing blood from a donor to the remainder of the tubing circuit 10. A blood return tubing assembly 30 provides a needle interface for returning blood components and other fluids to the donor. A single needle interface may also be used. Three lines 40, 42, 44 are provided in assembly 28 (see FIG. 3) for removal of blood from the donor. A cassette assembly 26 is connected between the tubing assembly 28, which connects to the donor, and blood inlet/blood component tubing line sub-assembly 32, which provides the interface between cassette assembly 26 and blood processing vessel 12. The cassette member 26 orients tubing segments in predetermined spaced relationships within the cassette member 26 for ultimate engagement with valve members on apharesis device 6. Such valves will, when activated, control flow through loops and tubing. Four lines 46, 48, 50 and 52 are shown in FIG. 2 and FIG. 3 for transport of blood and components to and from the processing vessel 12. An anticoagulant tubing assembly 30, a vent bag tubing line sub-assembly 34, a plasma collection tubing and bag assembly 36, and a white blood cell collection assembly 38 are also interconnected with cassette assembly 26. The extracorporeal tubing circuit 10 and blood processing vessel 12 are pre-connected to yield a closed, pre-sterilized disposable assembly for a single use.

When the tubing circuit 10 has been mounted on the blood component separation device 6, saline solution primes the tubing circuit through a saline line 54 and filter 56. Saline flows through an internal passageway 58 in the cassette 26 and through the line 40 to the distal end of the blood removal assembly 28. Saline can then flow up a blood withdrawal line 42 into the other tubes and passageways of the circuit 10 and up an anticoagulant line 44 in preparation for blood processing. A supply or bag (not shown) of anticoagulant connects to a distal end of the anticoagulant tubing assembly 30. Anticoagulant solution flows past a filter 60 and a first pump loop 62 through the anticoagulant line 44 to the distal end of the blood removal assembly. The pump loop 60 and other pump loops described herein couple with peristaltic pumps on the blood processing device 6 in a known manner. The device 6 controls the direction and rate of flow of the fluids described herein by controlling the speed and direction of the peristaltic pumps and the position of various valves.

AC solution from the anticoagulant line 44 mixes with the donor's blood in blood removal line 42. The blood removal line 42 conducts blood into the cassette 26, where the blood passes a first pressure sensor 63 and a second pump loop 64. A second pressure sensor 66, between second pump loop 64 with its associated pump and blood inflow line 68 to the blood processing vessel 12, senses the fluid pressure effective at an inlet to the blood processing vessel. The blood processing vessel will be described in greater detail below.

Emanating from vessel 12 is an RBC outlet tubing line 70 of the blood inlet/blood component tubing assembly 32. As shown in FIG. 3, the outlet tubing line 70 is interconnected with integral RBC passageway 72 of cassette assembly 26 and an external loop 74 to a return reservoir 76. The return reservoir 76 connects to sensors on the device 6 that detect low and high fluid levels. The device 6 keeps the fluid in the reservoir between these two levels by controlling flow out of the reservoir past a third or return pump loop 78 and a third or return pressure sensor 80. Fluid flows through an internal passageway 82 and into a return tube 84 in the blood return assembly 30. The return assembly 30 also comprises a saline line 86 connected internally in the cassette 26 to saline line 54 for priming as described above. As the primary object of this invention is the collection of white blood cells, red blood cells are not collected in the apparatus described herein, but are returned directly to the donor. This is because a large quantity of blood must be processed to collect a useful quantity of white blood cells. Indeed, additional replacement fluid may be added to the system for delivery to the donor through a replacement line 90 connected to the passageway 72. If desired, however, red blood cells could also be withdrawn through the replacement line 90 and collected.

As the fluid level in the reservoir 76 is constantly rising and falling, a vent bag 34 connects to the reservoir 76 through a vent tube 92. Air can flow between the reservoir 76 and the vent bag 34 in a sterile manner.

Plasma may also be collected from the blood processing vessel 12 into plasma bag 36. When desired, plasma is withdrawn from the blood processing vessel 12 through plasma line 94 and internal passageway 96 into a manifold 98 in the cassette 26. In the illustrated embodiment, a connecting tube 100 couples flow channels in the manifold 98, allowing plasma to flow through a second internal passageway 102 to a pump loop 104 and branching passageway 106. A valve (not shown) diverts the plasma either into a collect tube 108 to the plasma bag 36, or into a connecting loop 110 to the reservoir 76. Excess plasma in the reservoir 76 is returned to the donor in the same way as red blood cells, as described above.

In the present invention, white blood cells periodically flow out of the blood processing vessel 12 through a fourth or white blood cell line 112 in the tubing line sub-assembly 32. In the cassette 26, a passageway 114 connects the white blood cell line 112 to a red-green photo sensor 116. This sensor is used in connection with an algorithm, described below, to control periodic flushing of white blood cells out of the blood processing vessel 12 into the collect bag 38. The white blood cells flow from the sensor 116 through a fourth pump loop 118, which engages a peristaltic pump on the separation device 6. The fourth pump loop 118 connects to a valved passageway 120 in the cassette 28. The blood processing device 6 can control the valved passageway 120 to direct white blood cells either into a collect tube 122 and thence into the collect bag 38, or into a connection loop 124 and thence into the reservoir 76. Excess white blood cells in the reservoir 76 may be returned to the donor in the same way as red blood cells and plasma, as described above.

Most portions of the tubing assemblies 28, 30, 32, 36, 34, and 38 and cassette assembly 26 are made from plastic components including, for example, polyvinyl chloride (PVC) tubing lines, that may permit visual observation and monitoring of blood/blood components during use. Thin-walled PVC tubing may be employed for approved, sterile docking (i.e., the direct connection of two pieces of tubing line) for the RBC collector tubing lines 60. All tubing lines are pre-connected before sterilization of the total disposable assembly to assure that maximum sterility of the system is maintained. A highly desirable advantage of pre-connection of all of the elements of the tubing circuit including the collection bag sub-assembly 38 involves the complete pre-assembly and then sterilization hereof after pre-assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 60.

As mentioned, the cassette assembly 26 in the embodiment of FIG. 3 may be mounted upon and operatively interface with the pump/valve/sensor assembly 14 of a blood component separation device 6 during use. Further details of an apharesis system set-up including the loading and interaction of a disposable assembly 8 with a blood component separation device 6, may be found in the above-listed patents, and are not exhaustively repeated here.

Operation of Extracorporeal Tubing Circuit and Blood Component Separation Device Priming and various other operations of the apharesis process are carried out as set forth in the above-listed patents. During a blood removal, whole blood will be passed from a donor into tubing line 42 of blood removal tubing assembly 28 and is then transferred to blood component separation device 6. At device 6, the blood is pumped via pump loop 64 (FIG. 3), to the processing vessel 12 via the cassette assembly 26 and line 68 of the blood inlet/blood component tubing assembly 32. Separation processing then occurs on a substantially continuous basis in vessel 12, i.e., blood flows substantially continuously therein, is continuously separated and flows as separated components therefrom. After separation processing in vessel 12 (though separation is continuously occurring), uncollected blood components are transferred from the processing vessel 12 to and through cassette assembly 26, into and may then accumulate in reservoir 76 of cassette 26 up to a predetermined level at which the blood component separation device 6 may initiate a blood return submode wherein these uncollected and/or treated components may be returned to the donor through return line 84. As such, these accumulated components may be transferred into the blood return tubing line 24 of blood removal/return tubing assembly 28 and back into the donor. The cycle between blood removal and blood return submodes will then continue until a predetermined amount of white blood cells or other collected blood components have been harvested. In an alternative single needle scheme, as is known in the art, blood may be alternately removed from the donor and returned to a donor. The detailed mechanisms for such operations, including controlling the pumps, for example, are not shown or described in detail herein. Because a relatively large quantity of blood must be processed to isolate a suitable quantity of white blood cells, a dual needle configuration is preferred.

Figure 4:
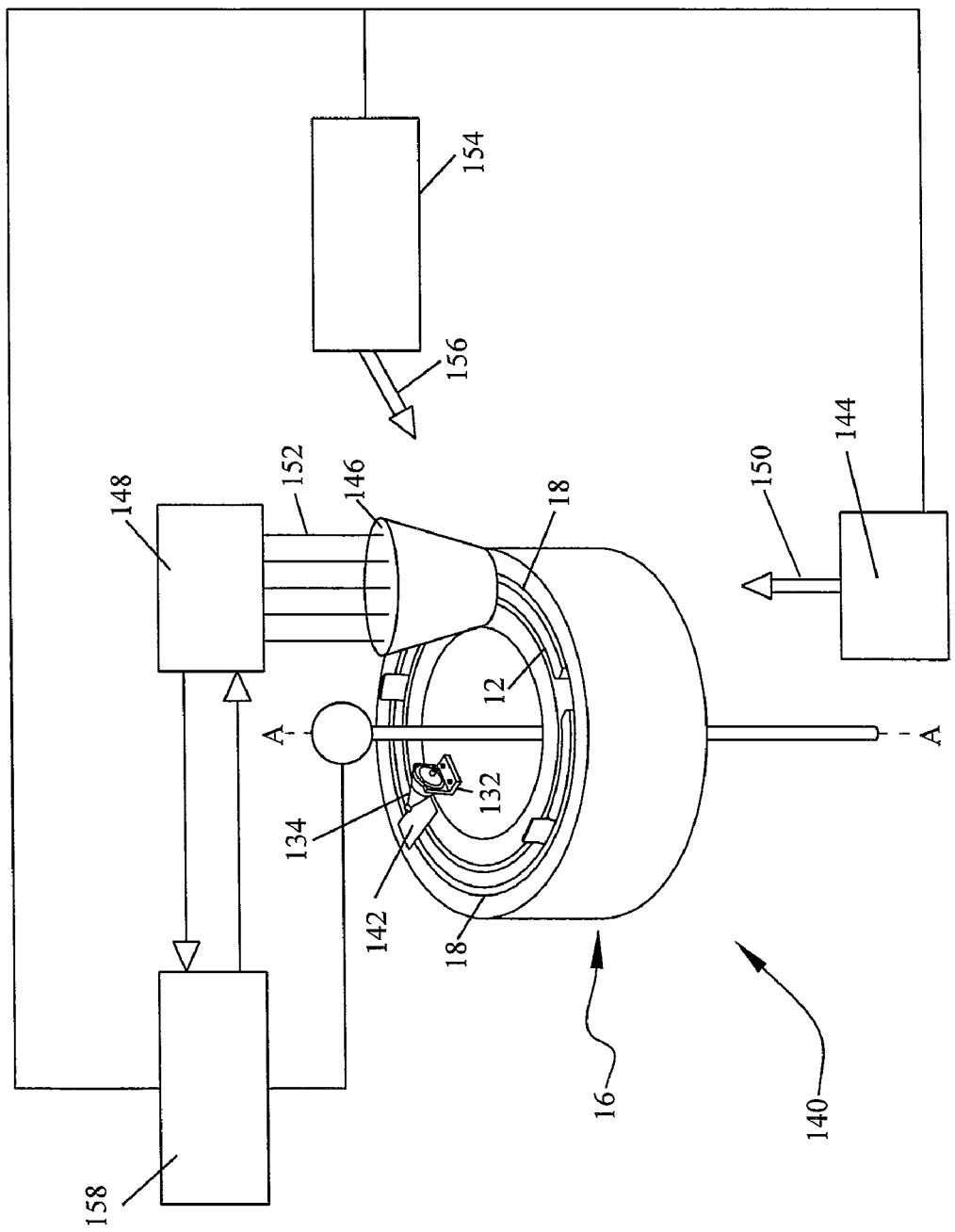
FIG. 4 is a partial perspective, schematic view of the centrifuge apparatus and a control camera.

As illustrated in FIG. 4, the centrifuge assembly 16 has a channel or annular groove 18 having an open upper surface adapted to receive a separation vessel 12, shown in FIG. 1. The channel 18 completely surrounds the rotor's axis of rotation A-A. A substantial portion of the channel 18 has a constant radius of curvature about the axis of rotation A-A and is positioned at a maximum possible radial distance on the centrifuge assembly 16. This shape ensures that substances separated in the separation vessel 12 undergo relatively constant centrifugal forces as they pass from an inlet portion to an outlet portion of the separation vessel 12.

A bracket 132 is provided on a top surface of the centrifuge assembly 16. The bracket 132 releasably holds a cell separation chamber 134 on the centrifuge assembly 16 so that an outlet 136 of the cell separation chamber 134 is positioned closer to the axis of rotation A-A than an inlet 138 of the chamber 134. The bracket 132 orients the chamber 134 on the centrifuge assembly 16 with a longitudinal axis of the cell separation chamber 134 in a plane transverse to the rotor's axis of rotation A-A. In addition, the bracket 132 is arranged to hold the cell separation chamber 134 on the centrifuge assembly 16 with the cell separation chamber outlet 136 facing the axis of rotation A-A. Although the chamber 134 is shown on a top surface of the centrifuge assembly 16, the chamber 134 could also be secured to the centrifuge assembly 16 at alternate locations, such as beneath the top surface of the centrifuge assembly 16.

FIG. 4 schematically illustrates an exemplary embodiment of an optical monitoring system 140 capable of measuring a distribution of scattered and/or transmitted light intensities corresponding to patterns of light originating from an observation region on the processing vessel 12. The monitoring system 140 comprises light source 144, light collection element 146, and detector or camera 148. Light source 144 is in optical communication with the centrifuge assembly 16, which rotates about central rotation axis A-A. Rotation about central rotation axis A-A results in separation of a blood sample in the processing vessel 12 into discrete blood components along a plurality of rotating separation axes oriented orthogonal to the central rotation axis A-A.

Light source 144 provides incident light beam 150, which stroboscopically illuminates an observation region 142 when the observation region 142 passes under the light collection element 146. Light source 144 is capable of generating an incident light beam, a portion of which is transmitted through at least one blood component undergoing separation in processing vessel 12. At least a portion of scattered and/or transmitted light 152 from the observation region 142 is collected by light collection element 146. Light collection element 146 is capable of directing at least a portion of the collected light 152 onto detector 148. The detector 148 detects patterns of scattered and/or transmitted light 152 from the observation region, thereby measuring distributions of scattered and/or transmitted light intensities. Distributions of scattered and/or transmitted light intensities comprise images corresponding to patterns of light originating from the observation region 142. The images may be monochrome images, which provide a measurement of the brightness of separated blood components along the separation axis. Alternatively, the images may be color images, which provide a measurement of the colors of separated blood components along the separation axis.

Figure 5:
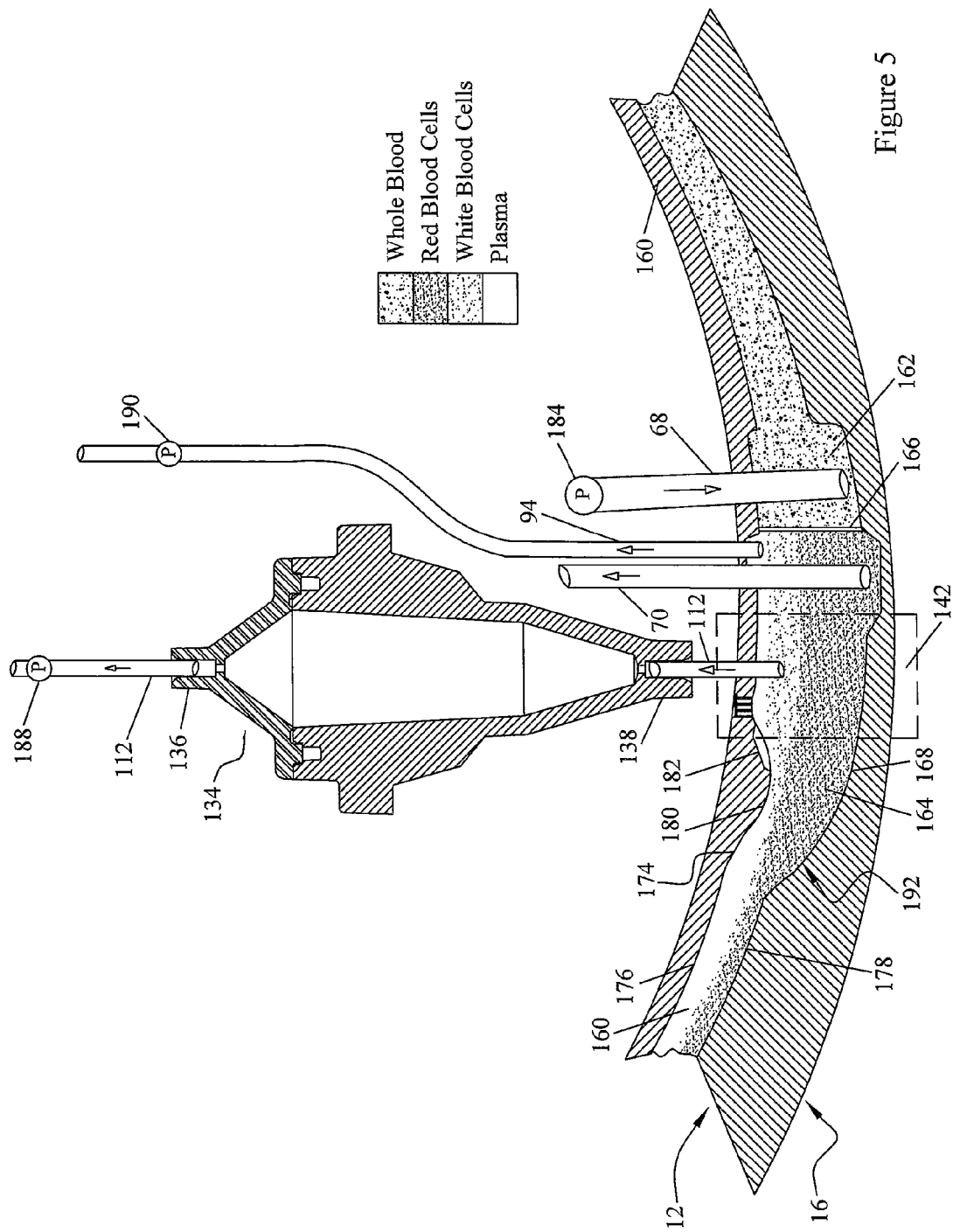
FIG. 5 is a partial cross-sectional, schematic view of a portion of a blood processing vessel and the cell separation chamber mounted on the centrifuge rotor of FIG. 1.
Figure 6:
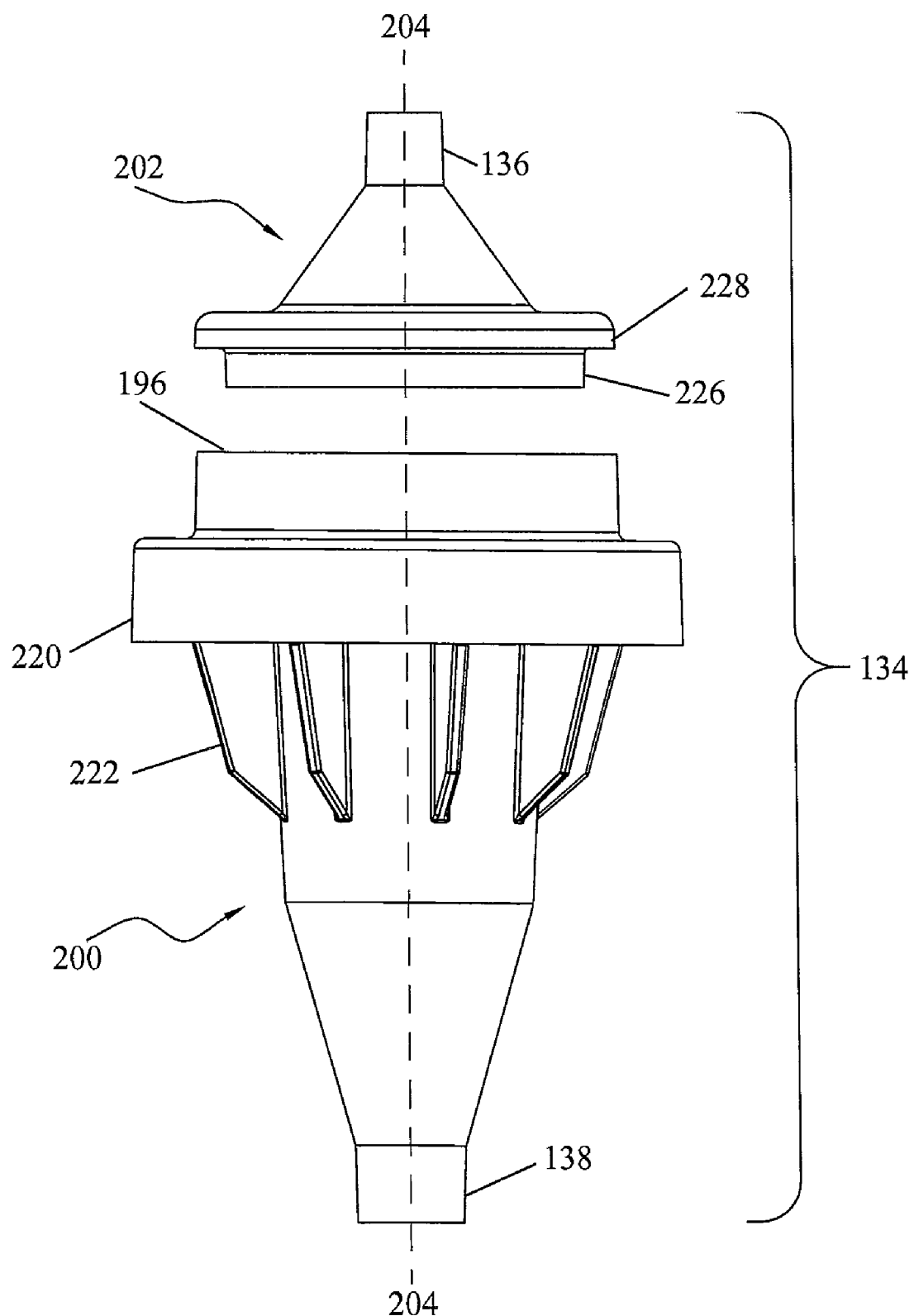
FIG. 6 is an exploded plan view of the cell separation chamber of FIG. 5.
Figure 7:
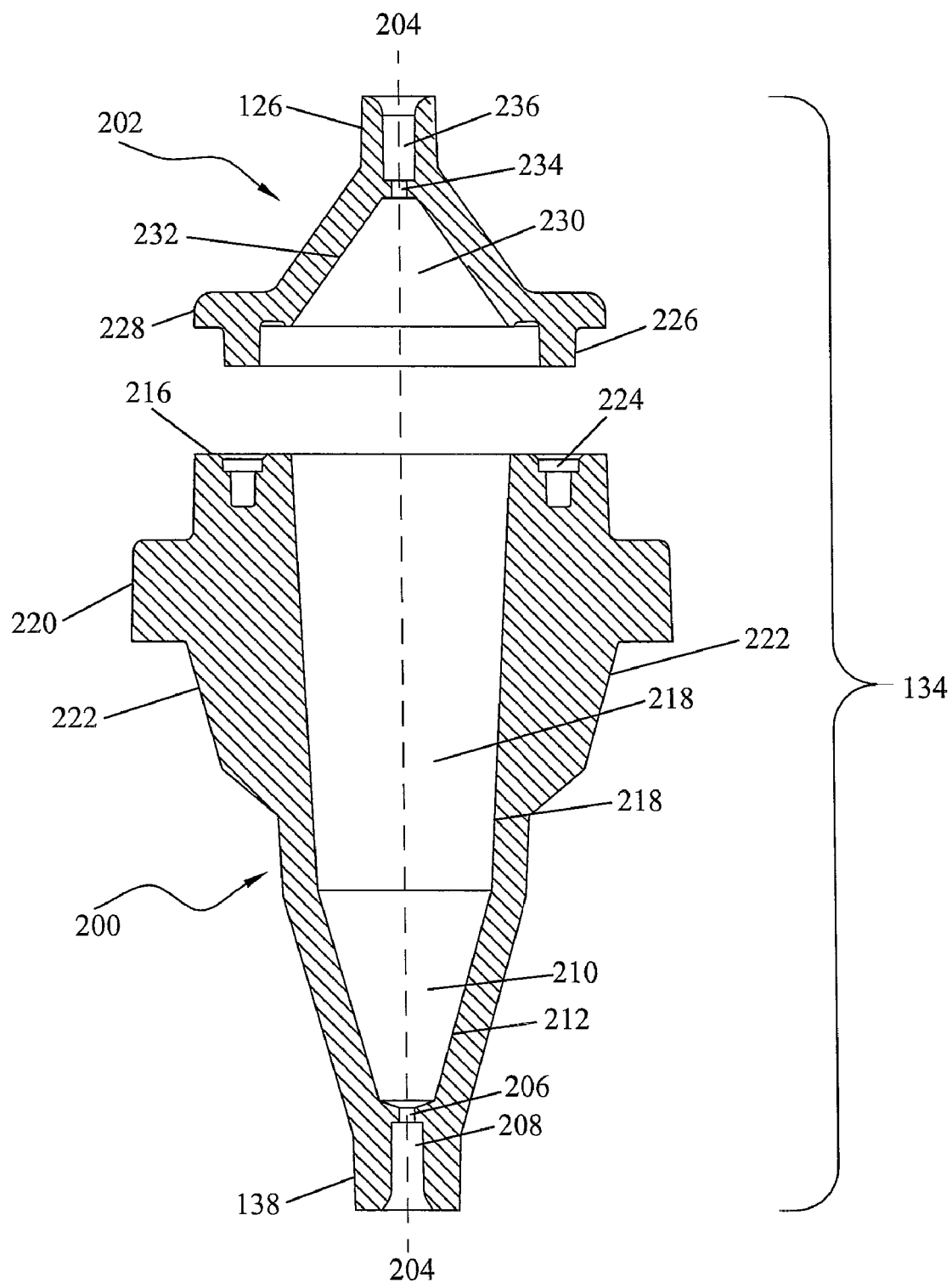
FIG. 7 is a cross-sectional view of the cell separation chamber of FIG. 6.

Observation region 142 is positioned on a portion of the processing vessel 12. As shown in FIG. 5, separated blood components and phase boundaries between optically differentiable blood components are viewable in observation region 142. Optionally, the observation region 142 may also be illuminated by an upper light source 154, which is positioned on the same side of the separation chamber as the light collection element 146 and detector 148. Upper light source 154 is positioned such that it generates an incident beam 156, which is scattered by the blood sample and/or centrifuge. A portion of the light from upper light source 154 is collected by light collection element 146 and detected by detector 148, thereby measuring a distribution of scattered and/or transmitted light intensities.

The detector 148 is also capable of generating output signals corresponding to the measured distributions of scattered and/or transmitted light intensities and/or images. The detector 148 is operationally connected to a device controller 158 capable of receiving the output signals. Device controller 158 displays the measured intensity distributions, stores the measured intensity distributions, processes measured intensity distributions in real time, transmits control signals to various optical and mechanical components of the monitoring system and centrifuge or any combination of these. Device controller 158 is operationally connected to centrifuge assembly 16 and separation device 6 and is capable of adjusting selected operating conditions of the separation device 6, such as the flow rates of cellular and non-cellular components out of the blood processing vessel 12 or cell separation chamber 134, the position of one or more phase boundaries, rotational velocity of the rotor about central rotation axis A-A, the infusion of anticoagulation agents or other blood processing agents to the blood sample, or any combination of these.

Device controller 158 can also be operationally connected to light source 144 and/or upper light source 154. The device controller 158 or the detector 148 are capable of generating output signals for controlling illumination conditions. For example, output signals from the detector 148 can be used to control the timing of illumination pulses, illumination intensities, the distribution of illumination wavelengths and/or position of light source 144 and/or upper light source 154. Device controller 158 and detector 148 are in two-way communication, and the device controller sends control signals to detector 148 to selectively adjust detector exposure time, detector gain and to switch between monochrome and color imaging.

Light sources comprise light emitting diode sources capable of generating one or more incident beams for illuminating the observation region. A plurality of lamps may be positioned to illuminate a single side or multiple sides of the centrifuge apparatus. Light emitting diodes and arrays of light emitting diode light sources are preferred for some applications because they are capable of generating precisely timed illumination pulses. Preferred light sources generate an incident light beam having a substantially uniform intensity, and a selected wavelength range.

FIG. 5 schematically illustrates a portion of the blood processing vessel 12 and cell separation chamber 134 mounted on the channel assembly 16. The blood processing vessel 12 has a generally annular flow path 160 and includes an inlet portion 162 and outlet portion 164. A wall 166 prevents substances from passing directly between the inlet and outlet portions 162 and 164 without first flowing around the generally annular flow path 160 (e.g., counterclockwise in FIG. 5). A radial outer wall 168 of the blood processing vessel 12 is positioned closer to the axis of rotation A-A in the inlet portion 162 than in the outlet portion 164. During separation of blood components, this arrangement causes formation of a very thin and rapidly advancing red blood cell bed in the processing vessel 12 between the inlet portion 162 and outlet portion 164. The red blood cell bed reduces the amount of blood components required to initiate a separation procedure, and also decreases the number of unnecessary red blood cells in the processing vessel 12. The red blood cell bed substantially limits or prevents platelets from contacting the radial outer wall 168 of the processing vessel 12. This is believed to reduce clumping of platelets caused when platelets contact structural components of centrifugal separation devices.

The inlet portion 162 includes an inflow tube 68 for conveying a fluid to be separated, such as whole blood, into the processing vessel 12. During a separation procedure, substances entering the inlet portion 162 follow the flow path 160 and stratify according to differences in density in response to rotation of the centrifuge assembly 16. The outlet portion 164 includes outlets for the RBC line 70, the plasma line 94, and white blood cell line 112 for removing separated substances from the separation vessel 12. Each of the components separated in the vessel 12 is collected and removed in only one area of the vessel 12, namely the outlet portion 164. In addition, the processing vessel 12 includes a substantially constant radius except in the region of the outlet portion 164 where the outer wall of the outlet portion 164 is positioned farther away from the axis of rotation A-A to allow for outlet ports of the lines 70, 94, and 112 to be positioned at different radial distances and to create a collection pool with greater depth for the high density red blood cells. The outlet port of line 70 is farther from the axis of rotation A-A than the other ports to remove higher density components, such as red blood cells. The port of line 94 is located closer to the axis of rotation A-A than the other ports to remove the least dense components separated in the processing vessel 12, such as plasma. The white blood cell line 112 collects intermediate density components and, in particular, white blood cells. The RBC and plasma lines 70 and 94 are positioned downstream from white blood cell line 112 to collect the high and low-density components.

The positions of the interfaces are controlled by the CCD camera 148 monitoring the position of the interface and controlling flow of liquid and/or particles in response to the monitored position. Further details concerning the structure and operation of the separation vessel 12 are described in U.S. patent application Ser. No. 10/884,877 and also in U.S. Pat. No. 4,094,461 to Kellogg et al. and U.S. Pat. No. 4,647,279 to Mulzet et al., which have been incorporated herein by reference.

A ridge 174 extends from the inner wall 176 of the channel 18 toward the outer wall 178 of the groove 18. When the blood processing vessel 12 is loaded in the channel 18, the ridge 174 deforms semi-rigid or flexible material in the outlet portion 164 of the separation vessel 12 to form a trap dam 180 in the separation vessel 12, upstream from the first line 170. The trap dam 180 extends away from the axis of rotation A-A to trap a portion of lower density substances, such as priming fluid and/or plasma, along an inner portion of the separation vessel 12 located upstream the trap dam 180. These trapped substances help convey platelets to the outlet portion 164 and white blood cell line 112 by increasing plasma flow velocities next to the layer of red blood cells in the blood processing vessel 12 to scrub platelets toward the outlet portion 164. A downstream portion 182 of the trap dam 180 has a relatively gradual slope extending in the downstream direction toward the axis of rotation A-A, which limits the number of platelets (intermediate density components) that become re-entrained (mixed) with plasma (lower density components) as plasma flows along the trap dam 180. In addition, the gradual slope of the downstream portion 182 reduces the number of platelets that accumulate in the processing vessel 12 before reaching the white blood cell line 112.

The camera 148 is generally focused on the separation vessel and stroboscopic illumination allows an observation region 142 around the outlets for lines 70, 94 and 112 to be observed. Using information gathered through the camera, the controller 158 regulates the position of interfaces between various blood components, such as plasma, buffy coat (containing monocytes and/or white blood cells and platelets) and red blood cells by controlling pumps 184, 188, and 190, described below.

Referring again to FIG. 5, the outer wall 178 of the channel 18 includes a gradual sloped portion 192 facing the ridge 174 in the inner wall 176. When the processing vessel 12 is loaded in the channel 18, the gradual sloped portion 192 deforms semi-rigid or flexible material in the outlet portion 164 of the processing vessel 12 to form a relatively smooth and gradual sloped segment in a region of the vessel 12 across from the trap dam 180, which slopes gradually away from the axis of rotation A-A to increase the thickness of a layer of high-density fluid components, such as red blood cells, formed across from the trap dam 180.

The outlet of the white blood cell line 112 is connected to the cell separation chamber inlet 138 to pass the intermediate density components, including white blood cells, into the cell separation chamber 134. Components initially separated in the separation vessel 12 are further separated in the cell separation chamber 134. For example, white blood cells could be separated from plasma and platelets in the cell separation chamber 134. This further separation takes place by forming a saturated fluidized bed of particles, such as white blood cells, in the cell separation chamber 134. The cell separation chamber 134 may be formed of a transparent or translucent co-polyester plastic, such as PETG, to allow viewing of the contents within the chamber interior with the aid of the camera during a separation procedure.

As schematically shown in FIG. 4, a plurality of pumps 184, 188, and 190 are provided for adding and removing substances to and from the blood processing vessel 12 and cell separation chamber 134. An inflow pump 184 is coupled to the inflow line 46 to supply the substance to be separated, such as whole blood, to the inlet portion 162. In addition, a first collection pump 188 is flow coupled to the white blood cell line 112 connected to the cell separation chamber outlet, and a second collection pump 190 is flow coupled to the plasma collection line 94. The first collection pump 188 draws liquid and particles from the cell separation chamber outlet 136 and causes liquid and particles to enter the cell separation chamber 134 via the cell separation chamber inlet 138. The second collection pump 190, on the other hand, removes primarily low-density substances from the separation vessel 12 via the plasma line 94. The pumps 184, 188, and 190 are peristaltic pumps or impeller pumps configured to prevent significant damage to blood components. However, any fluid pumping or drawing device may be provided. The pumps 184, 188, and 190 may be mounted at any convenient location. The device 6 further includes the controller 158 connected to control rotational speed of the channel assembly 16. The controller 158 is connected to the pumps 184, 188, and 190 to control the flow rate of substances flowing to and from the blood processing vessel 12 and the cell separation chamber 134. The controller 158 maintains a saturated fluidized bed of first particles within the cell separation chamber 134 to cause second particles to be retained in the cell separation chamber 134. The controller 158 also controls the operation and flow rate of the pumps 184, 188, 190 to permit the temporary purging of the cell separation chamber 134. The controller 158 may include a computer having programmed instructions provided by a ROM or RAM as is commonly known in the art. The controller 158 may receive input from a rotational speed detector (not shown) to constantly monitor the rotation speed of the rotor.

After loading the blood processing vessel 12 and cell separation chamber 134 on the channel assembly 16, the blood processing vessel 12 and separation chamber 134 are initially primed with a low density fluid medium, such as saline solution, plasma, or another fluid substance having a density less than or equal to the density of liquid plasma. Alternatively, the priming fluid is whole blood itself. As the processing vessel 12 rotates, a portion of the priming fluid (blood or saline solution) becomes trapped upstream from the trap dam 180 and forms a dome of priming fluid (plasma or saline solution) along an inner wall of the separation vessel 12 upstream from the trap dam 180. After the tubing circuit 10 is primed, and as the centrifuge assembly 16 rotates, whole blood or blood components are introduced into the blood processing vessel 12. When whole blood is used, the whole blood can be added to the processing vessel 12 by transferring the blood directly from a donor or patient through inflow line 68. In the alternative, the blood may be transferred from a container, such as a blood bag, to inflow line 68.

The blood within the processing vessel 12 is subjected to centrifugal force causing components of the blood components to separate. The components of whole blood stratify in order of decreasing density as follows: (1) red blood cells, (2)

white blood cells, (3) platelets, and (4) plasma. The controller 158 regulates the rotational speed of the centrifuge channel assembly 16 to ensure that this particle stratification takes place. A layer of red blood cells (high density components) forms along the outer wall of the processing vessel 12 and a layer of plasma (lower density components) forms along the inner wall of the processing vessel 12. Between these two layers, the intermediate density platelets and white blood cells (intermediate density components) form a buffy coat layer. This separation takes place while the components flow from the inlet portion 162 to the outlet portion 164. The radius of the flow path 160 between the inlet and outlet portions 162 and 164 is substantially constant to maintain a steady red blood cell bed in the outlet portion 164, even if flow changes occur.

In the outlet portion 164, platelet-poor plasma flows through the third line 94. These relatively low-density substances are pumped by the second collection pump 190 through the plasma collection line 94. Red blood cells are removed via the RBC line 70. The red blood cells flow through the RBC line 70 and can then be returned to the donor or, alternatively, collected and optionally recombined with other blood components or further separated. Accumulated white blood cells are removed via the white blood cell line 112, along with platelets and plasma. As the platelets, plasma, white blood cells, and possibly a small number or red blood cells pass through the line 112, these components flow into the cell collection chamber 134, filled with the priming fluid, so that a saturated fluidized particle bed may be formed. The portion or dome of priming fluid (i.e. saline) trapped along the inner wall of the blood processing vessel 12 upstream from the trap dam 180 guides platelets so that they flow toward the white blood cell line 112. The trapped fluid reduces the effective passageway volume and area in the processing vessel 12 and thereby decreases the amount of blood initially required to prime the system in a separation process. The reduced volume and area also induces higher plasma and platelet velocities next to the stratified layer of red blood cells, in particular, to "scrub" platelets toward the white blood cell line 112. The rapid conveyance of platelets increases the efficiency of collection.

The controller 158 maintains the rotation speed of the centrifuge assembly 16 within a predetermined rotational speed range to facilitate formation of this saturated fluidized bed. In addition, the controller 158 regulates the pump 188 to convey at least the plasma, platelets, and white blood cells at a predetermined flow rate through the white blood cell collection line 112 and into the inlet 138 of the cell separation chamber 134. These flowing blood components displace the priming fluid from the cell separation chamber 134. When the platelet and white blood cell particles enter the cell separation chamber 134, they are subjected to two opposing forces. Plasma flowing through the cell separation chamber 134 with the aid of pump 188 establishes a first viscous drag force when plasma flowing through the cell separation chamber 134 urges the particles toward the outlet 136. A second centrifugal force created by rotation of the channel assembly 16 and cell separation chamber 134 acts to urge the particles toward the inlet 138. The controller 158 regulates the rotational speed of the centrifuge assembly 16 and the flow rate of the pump 188 to collect platelets and white blood cells in the cell separation chamber 134. As plasma flows through the cell separation chamber 134, the flow velocity of the plasma decreases and reaches a minimum as the plasma flow approaches the maximum cross-sectional area of the cell separation chamber 134. Because the rotating centrifuge assembly 16 creates a sufficient gravitational field in the cell separation chamber 134, the platelets accumulate near the maximum cross-sectional area of the chamber 134, rather than flowing from the chamber 134 with the plasma. The white blood cells accumulate somewhat radially outward from the maximum cross-sectional area of the chamber 134. However, density inversion tends to mix these particles slightly during this initial establishment of the saturated fluidized particle bed.

The cell separation chamber 134 is configured to allow cyclic collection of selected particles, such as white blood cells, followed by efficient evacuation of the cells into a collection bag. The cell separation chamber 134 may be constructed in two pieces, a main body 200 and a cap 202, both being symmetrical around an axis 204. The main body 200 has an inlet 138 comprising a through bore 206 and a concentric stopped bore 208. The diameter of the through bore 206 corresponds to the inside diameter of the white blood cell line 112, while the diameter of the stopped bore 208 corresponds to the outside diameter of the line 112, so that the white blood cell line 112 can be seated in the stopped bore 208 and a fluid passageway of constant diameter can be formed between the line 112 and the through bore 206. The through bore 206 opens into a first frustoconical segment 210. A wall 212 of the first frustoconical segment 210 tapers away from the axis 204. Immediately adjacent to and down stream from the first frustoconical segment 210, a second frustoconical segment 214 extends from the first frustoconical segment 210 to a distal end 216 of the main body 200. A wall 218 of the second frustoconical segment 214 tapers away from the axis 204. Particles are pushed through the first segment by fluid flow, gradually slowing as the flow rate diminishes. In the second segment 214, the particles experience substantially constant forces. By altering either the rate of rotation or the fluid flow rate or both the countervailing forces of fluid pushing in and centripetal force pushing out can be balanced for the particular particle of interest. The selected particles begin to enter the cell separation chamber 134.

In the illustrated embodiment, the main body 200 of the cell separation chamber 134 further comprises a circumferential flange 220, which is supported in the holder 132. Radial fins 222 are formed proximally from the flange 220. The fins serve primarily for stability when the cell separation chamber 134 is mounted in an existing holder and also as conduits for plastic material during injection molding of the main body 200. At the distal end 216 of the main body 200, a groove 224 secures the cap 202 to the distal end. The cap comprises a rim 226 that fits into the groove 224 and a flange 228 which fits against the distal end of the main body. The cap and main body may be joined by ultrasonic welding, or other suitable techniques as known in the art. The cap opens into an abrupt frustoconical segment 230. The abrupt segment 230 tapers towards the axis 204, the inner wall 232 of the abrupt segment 230 forming an angle with the axis 204. The abrupt segment 230 funnels collected blood components flushed from the second segment 214 into the outlet 136 without excessive turbulence or damage to the blood components. The outlet 136 comprises a through bore 234 and a concentric stopped bore 236. The diameter of the through bore 234 corresponds to the inside diameter of the white blood cell line 112, while the diameter of the stopped bore 236 corresponds to the outside diameter of the white blood cell line 112, so that the line 112 can be seated in the stopped bore 236 and a fluid passageway of constant diameter can be formed between the line 112 and the through bore 234. The through bore 234 opens into the frustoconical segment 230.

The cell separation chamber 134 described above is particularly effective for collecting blood components such as white blood cells. Collection of such relatively rare blood components requires length donation times, during which portions of the donor's blood are repeatedly withdrawn from the donor, processed to capture the white blood cells, and returned to the donor. A typical donation session may last two to three hours. The present invention provides means for detecting when the cell separation chamber 134 has filled with white blood cells, flushing the white blood cells out of the cell separation chamber 134 into a collect bag 38, and resuming collection of white blood cells in the cell separation chamber 134. The red-green sensor 116 senses the optical characteristics of the fluid leaving the cell separation chamber 134. The device 6 calculates a baseline value characteristic of the particular donor. The device also calculates a red-green ratio of the intensities of red light and green light and a peak-to-peak ratio of intensities. If either the red-green ratio or the peak-to-peak ratio exceeds thresholds computed from the baseline value, the device increases flow through the cell separation chamber 134, causing the white blood cells to be flushed into the collect bag 38. In addition, the camera detects white cells passing into the cell separation chamber 134 and the device calculates the number of cells being collected. If the calculated number of collected cells exceeds a certain limit, the cell separation chamber is flushed, even though neither the threshold of the red-green ratio nor the threshold of the peak-to-peak ratio has been exceeded. In addition, if the device is unable to establish a baseline, the donation can proceed, relying solely on the calculated number of collected cells. This process will be explained more fully in connection with the attached graphs and computer software flowcharts.

Figure 8:
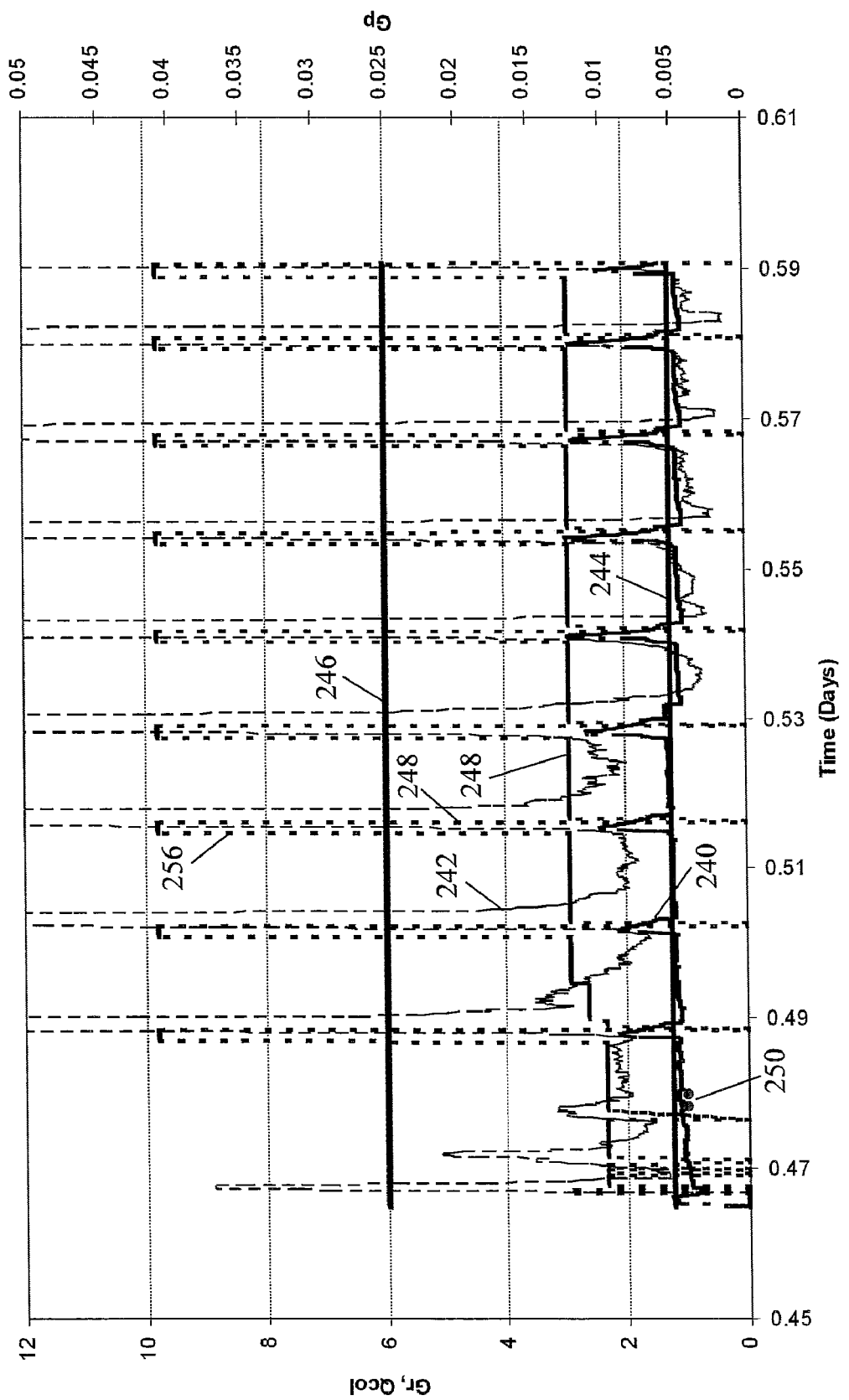
FIG. 8 is a graph of signals for control of a cell capture chamber trigger.

FIG. 8 shows signals for both the red-green ratio 240 and the peak-to-peak ratio 242 compared to a red-green ratio threshold 244 and a peak-to-peak ratio threshold 246. The flow rate 248, Qcol, through the cell separation chamber 134 is also shown. FIG. 8 represents a typical donation cycle, extending over 0.12 days, that is, about 3 hours. Nine collection cycles are shown wherein white blood cells are flushed into the collect bag 38. During an initial period indicated on the graph by two dots 250, the device attempts to establish baseline values for the signals received for a particular donor. If the signals are sufficiently stable (as will be explained below), the red-green ratio threshold 244 and the peak-to-peak ratio threshold 246 are set. If either the red-green ratio 240 crosses its threshold 244 or the peak-to-peak ratio 242 crosses its threshold 246, the device increases the fluid flow through the cell separation chamber 134 and directs the contents into the collect bag 38. In the illustrated example, the red-green ratio 240 crosses its threshold first. For other donors, the peak-to-peak ratio may be controlling, or may serve as a secondary control, if the red-green ratio is not sensed during a particular cycle.

Figure 9:
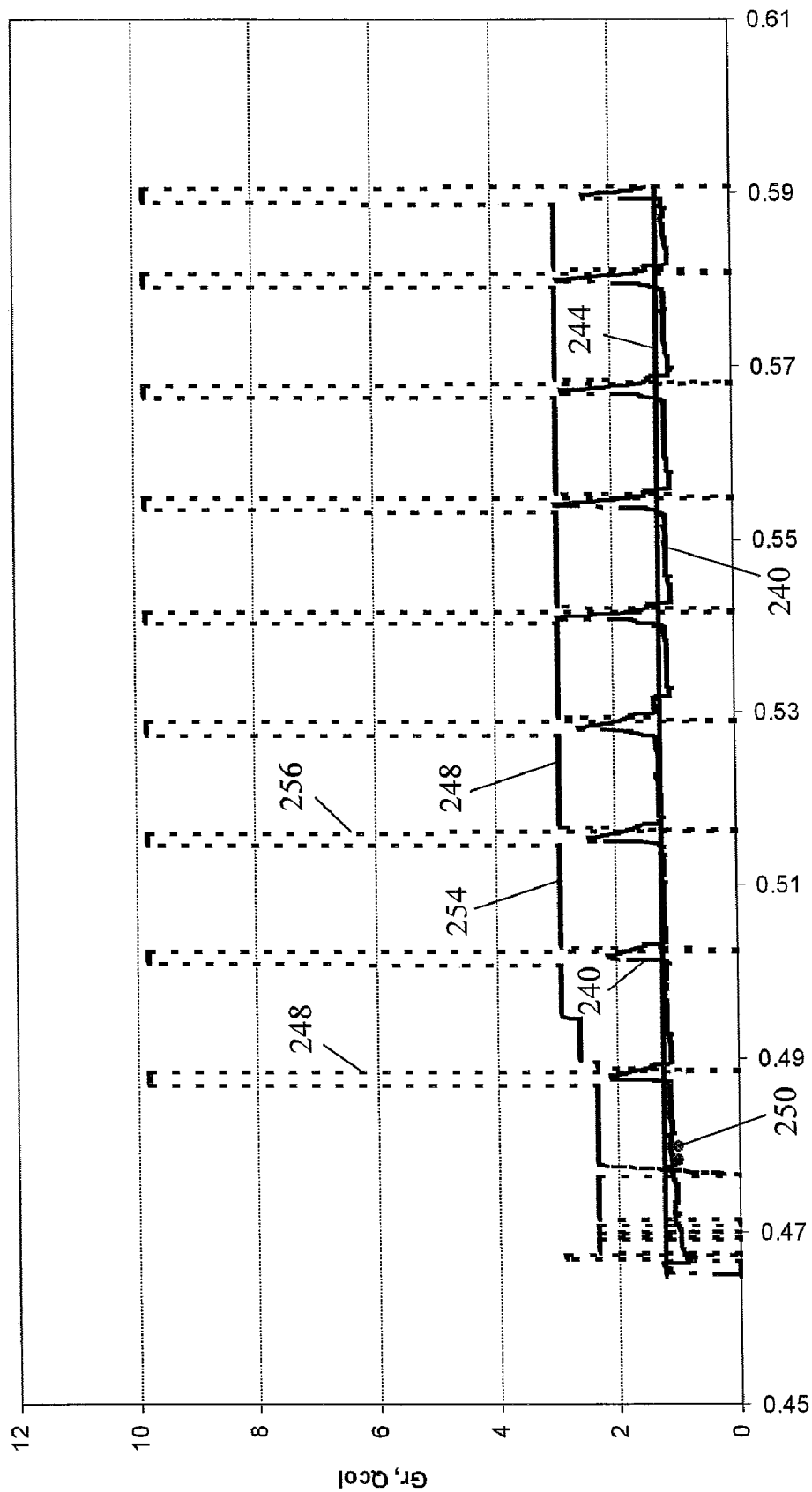
FIG. 9 is a graph of selected signals of FIG. 8 related to a red-green ratio trigger.
Figure 10:
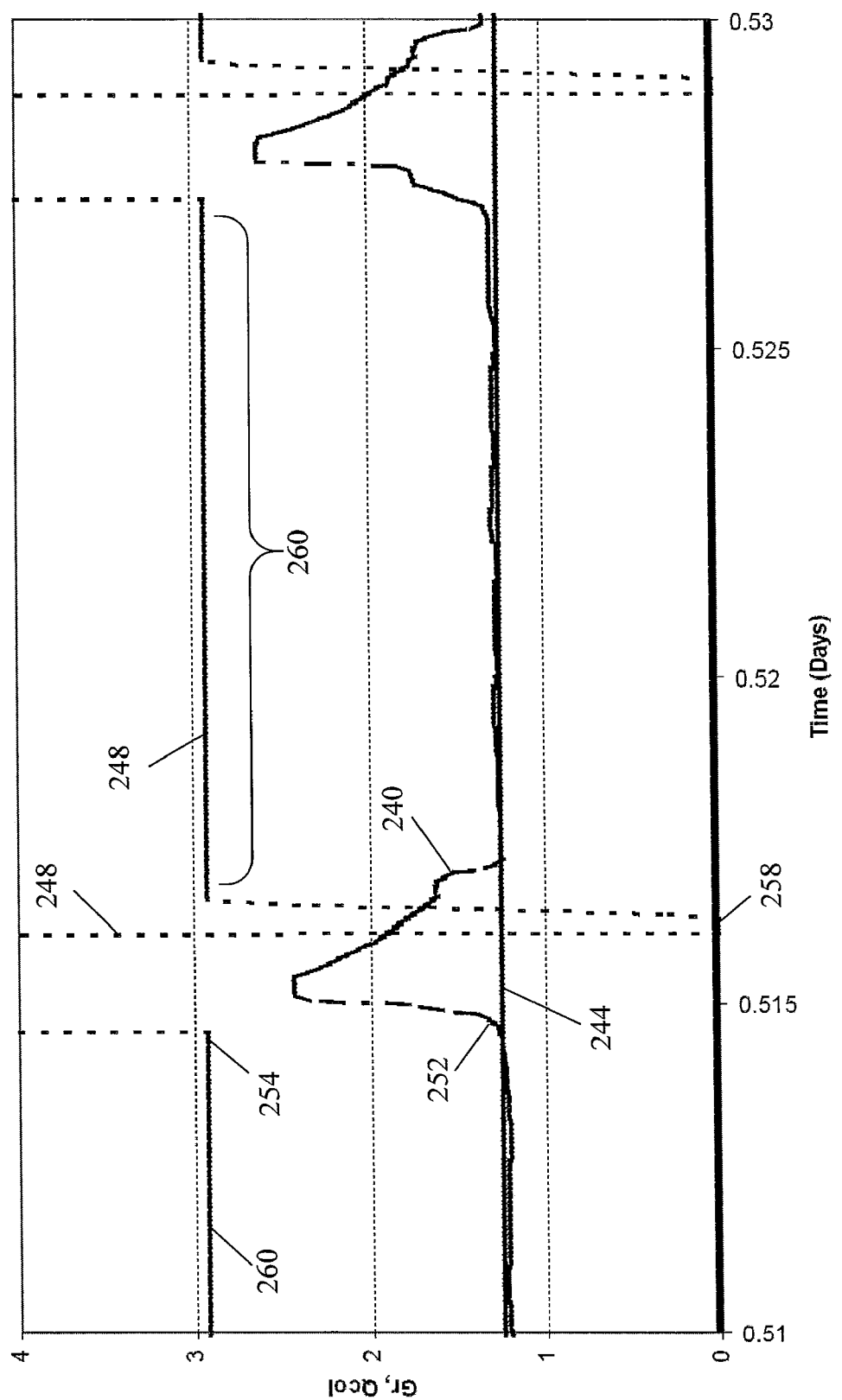
FIG. 10 is an enlarged section of the graph of FIG. 9.

For clarity, FIG. 9 and FIG. 10 show only the red-green ratio 240, the red-green threshold 244 and the flow rate 248. As seen in FIG. 10, when the cell collection chamber 134 has become sufficiently filled with white blood cells, the red-green ratio 240 crosses the threshold 244 at point 252. The device 6 increases the fluid flow rate 248 at 254 by controlling pump speeds and other parameters. The fluid flow rate 248 increases sharply to a maximum 256, which is maintained for about three minutes. The fluid flow rate is then reduced momentarily to zero 258 before being restored to a constant rate 260. The cell separation chamber begins to collect more white blood cells, and the cycle is repeated.

Figure 11:
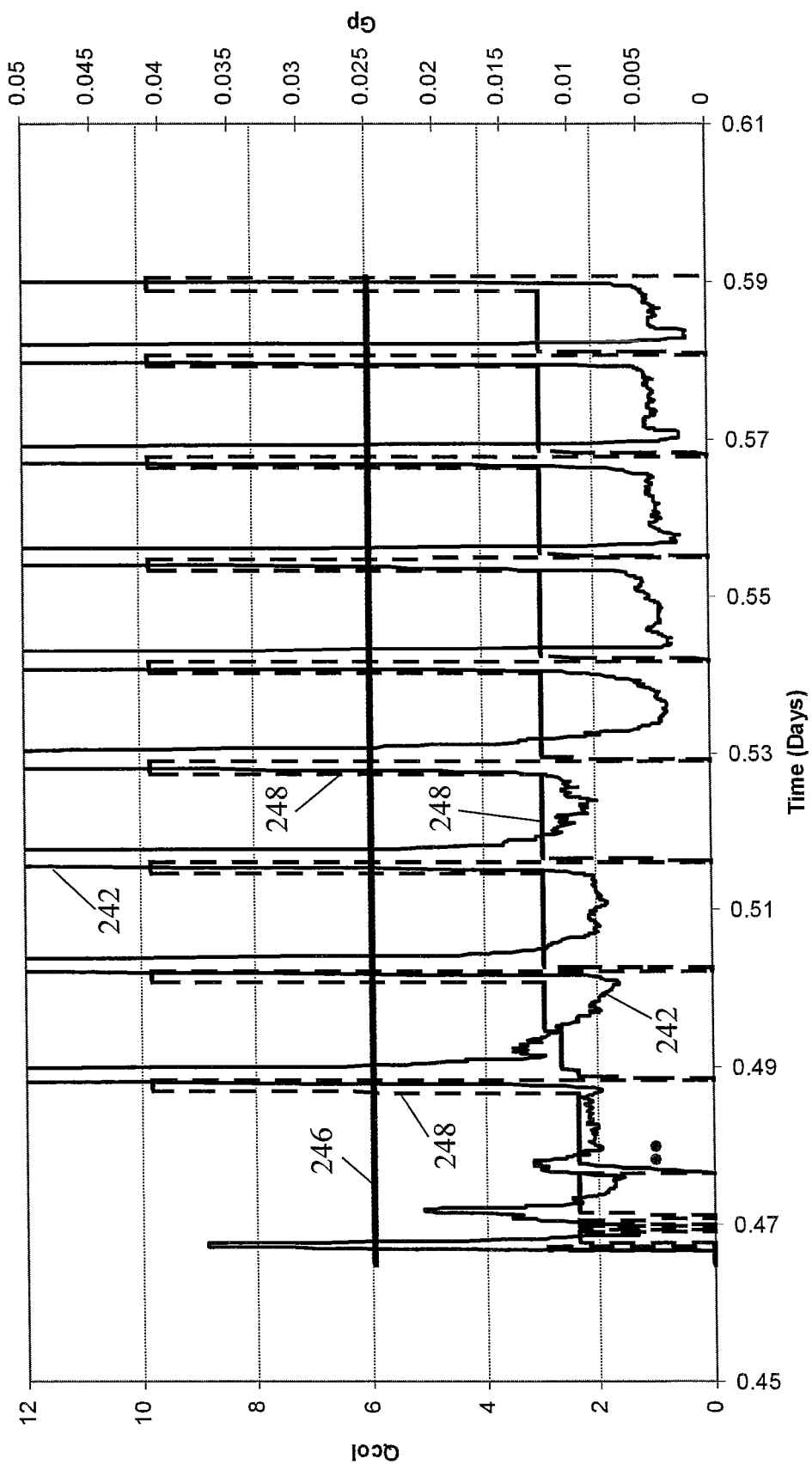
FIG. 11 is a graph of selected signals of FIG. 8 related to a peak-to-peak trigger.
Figure 12:
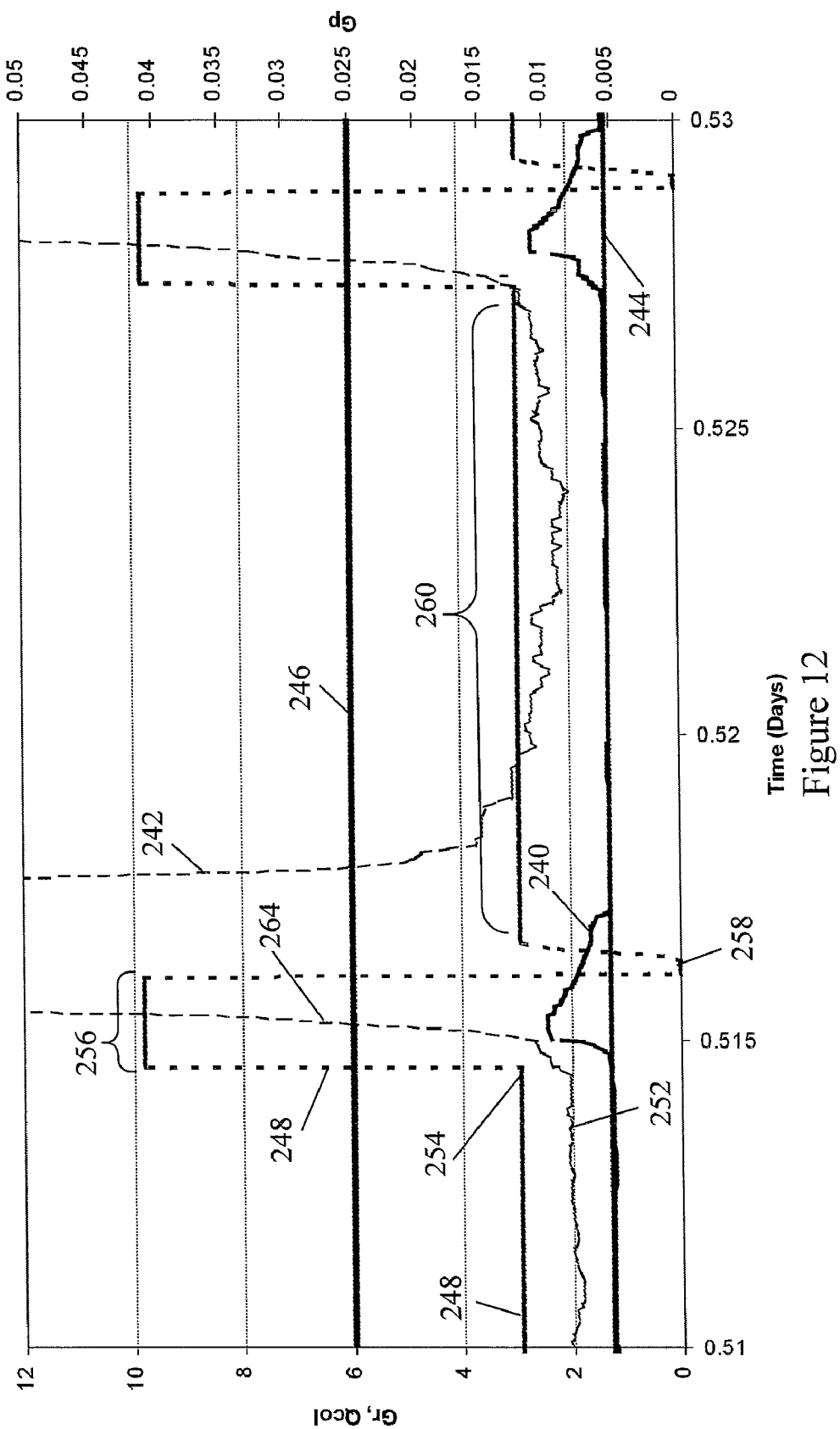
FIG. 12 is an enlarged section of the graph of FIG. 11.

In FIG. 11 and FIG. 12, the peak-to-peak ratio 242 does not trigger a white blood cell collection, although it could do so for a particular donor, in the same manner as the red-green ratio. In response to the increase in fluid flow at point 254, the peak-to-peak ratio 242 begins to increase at point 262 and crosses the peak-to-peak threshold 246 at point 264. Since the fluid flow is already increased to a maximum 256, the fluid flow is not changed. Otherwise, crossing the threshold at 264 would trigger increased fluid flow and flushing of the cell separation chamber 134. After fluid flow is reduced, the peak-to-peak ratio falls as collection conditions are restored during constant flow 260.

The device 6 has a third method for triggering flushing of the cell separation chamber 134. In addition to the red-green sensor 116 in the outflow line of the cell separation chamber, the camera 148 can detect blood components in the line 160, which is an inflow line into the chamber. As explained in greater detail in U.S. application Ser. No. 11/774,073, incorporated herein by reference, the camera 148 is generally focused on the blood processing vessel 12 and stroboscopic illumination allows the observation region 142 to be observed. Using information gathered through the camera, the controller 158 regulates the position of interfaces between various blood components, such as plasma, buffy coat (containing monocytes and/or white blood cells and platelets) and red blood cells by controlling the pumps 184, 188, and 190. FIG. 5 shows an image of the observation region 142 corresponding to the separation of a human blood sample and extraction of a separated white blood cell-containing blood component. The observation region 142 shown in FIG. 5 includes a phase boundary monitoring region and an extraction or collect port monitoring region. Visible in phase boundary monitoring region are a red blood cell component, a plasma component and a mixed-phase buffy coat layer, which has both white blood cells and platelets. Several calibration markers are also apparent in the image in FIG. 5. Calibration markers are used to indicate the positions and physical dimensions of the phase boundary monitoring region and the white blood cell collect port monitoring region. The physical dimension may be determined by adjusting the optics to within a selected range and then configuring the software with a parameter to convert pixels to microns. Alternatively, the thickness of the optical reference, usually about 1 mm, could be used. Light intensities transmitted through the phase boundary monitoring region are acquired as a function of time and analyzed in real time to provide measurements of the position of the phase boundary between red blood cell component and buffy coat layer and the phase boundary between the buffy coat layer and plasma component. All boundary layer positions are measured relative to the edge of the optical reference.

Collect port monitoring region monitors flow in white blood cell line 112 of the optical cell for extracting a blood component, for example, white blood cells. The apparatus responds to changes in detected blood component flow to establish a correct phase boundary level and further responds to changes in observed phase boundaries to maintain a consistent phase boundary level. The system discriminates between a plasma flow condition, a white blood cell flow condition, and a red blood cell flow condition, and can detect pump-induced flow variation in the blood component flow in said collect port measuring area. A plasma signal limit and a red blood cell signal limit may be set and the flow of fluid adjusted based on said limits. The system derives a statistical measure of fluid flow in the collect port measuring area, which may be a moving median of the average value of intensity of pixels in the collect port measuring area.

In this example, white blood cell line 112 is configured to collect white blood cells in the human blood sample and extends a distance along the separation axis such that it terminates proximate to the buffy coat layer in the rotating separation chamber. The two-dimensional distribution of light intensities of light transmitted through the collect port in the collect port monitoring region depends on the concentration, and spatial distribution and cell-type of cellular material exiting the separation chamber. Light intensities transmitted through the collect port monitoring region are acquired as a function of time and analyzed to characterize the composition and flux of cellular material out of the separation chamber. As cellular materials, such as white blood cells and red blood cells, absorb and scatter light from the light sources, passage of cellular material through the extraction port decreases the observed light intensities.

The device 6 estimates the number of white cells flowing into the chamber 138 by imaging the cells in the line 112. From the known volume of the chamber and a representative size of white blood cells, the device can estimate the quantity of white blood cells in the chamber. If the estimated quantity is too low when a trigger event from either the red-green ratio or the peak-to-peak ratio is detected, for example 50% of the estimated capacity, the trigger event may be disregarded as a false positive. If the estimated quantity is too high before a trigger event is detected, for example 150% of the estimated capacity, the chamber may be flushed on the assumption that the trigger event had not been detected either because of an error in sensing or an incorrect threshold. If the conditions were not stable enough to set a baseline, with associated thresholds, the chamber 134 may be flushed at a selected estimated capacity, for example 105% of the estimated capacity. Control by estimating the number of white cells viewed by the camera and captured in the chamber is thus less sensitive to initial conditions and less precise in responding to actual filling of the cell separation chamber. Consequently, white blood cells can be harvested more efficiently using the red-green ratio and the peak-to-peak ratio as triggers.

Figure 13A:
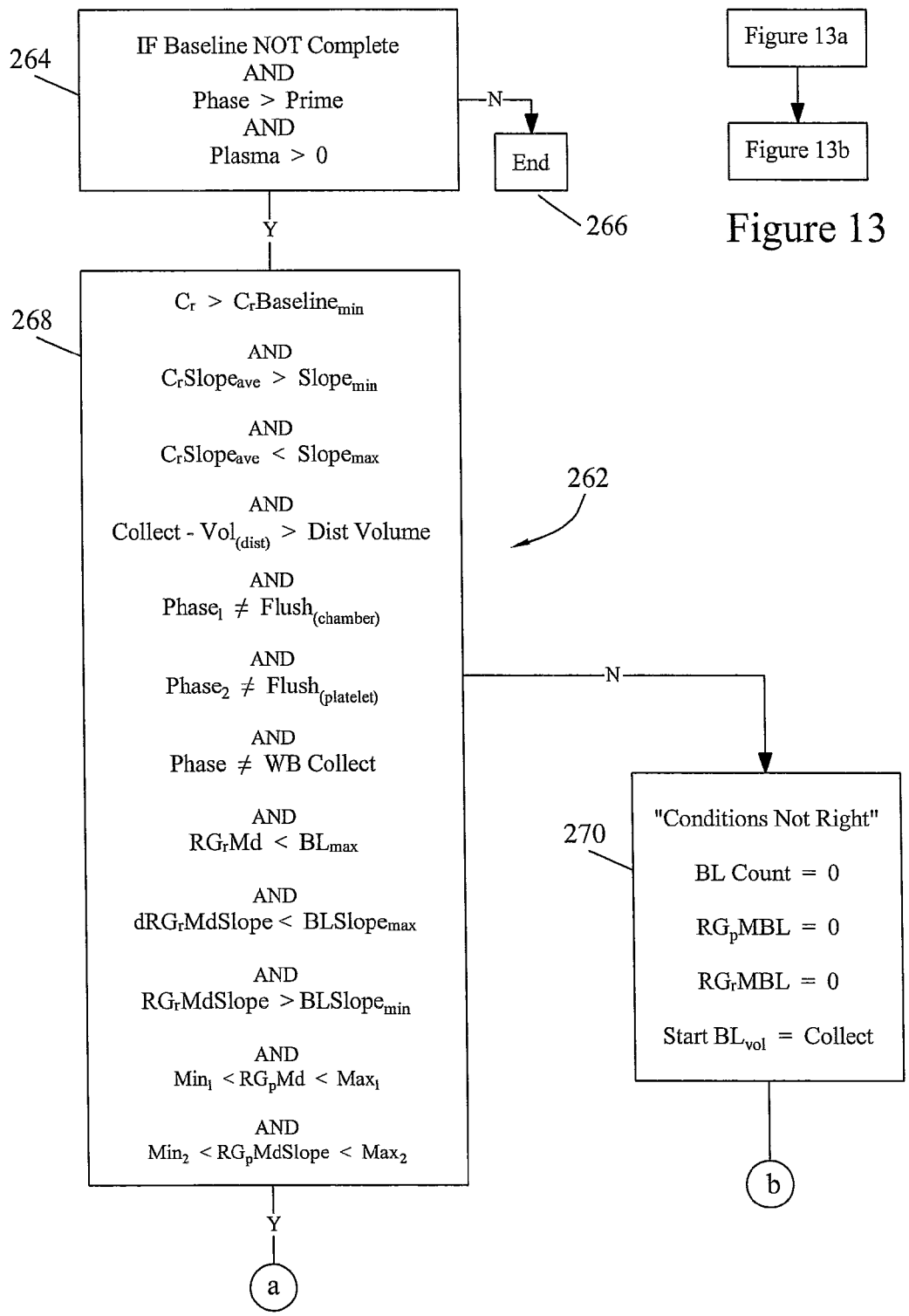
FIG. 13 is a flow chart of an algorithm for establishing baseline values.
Figure 13B:
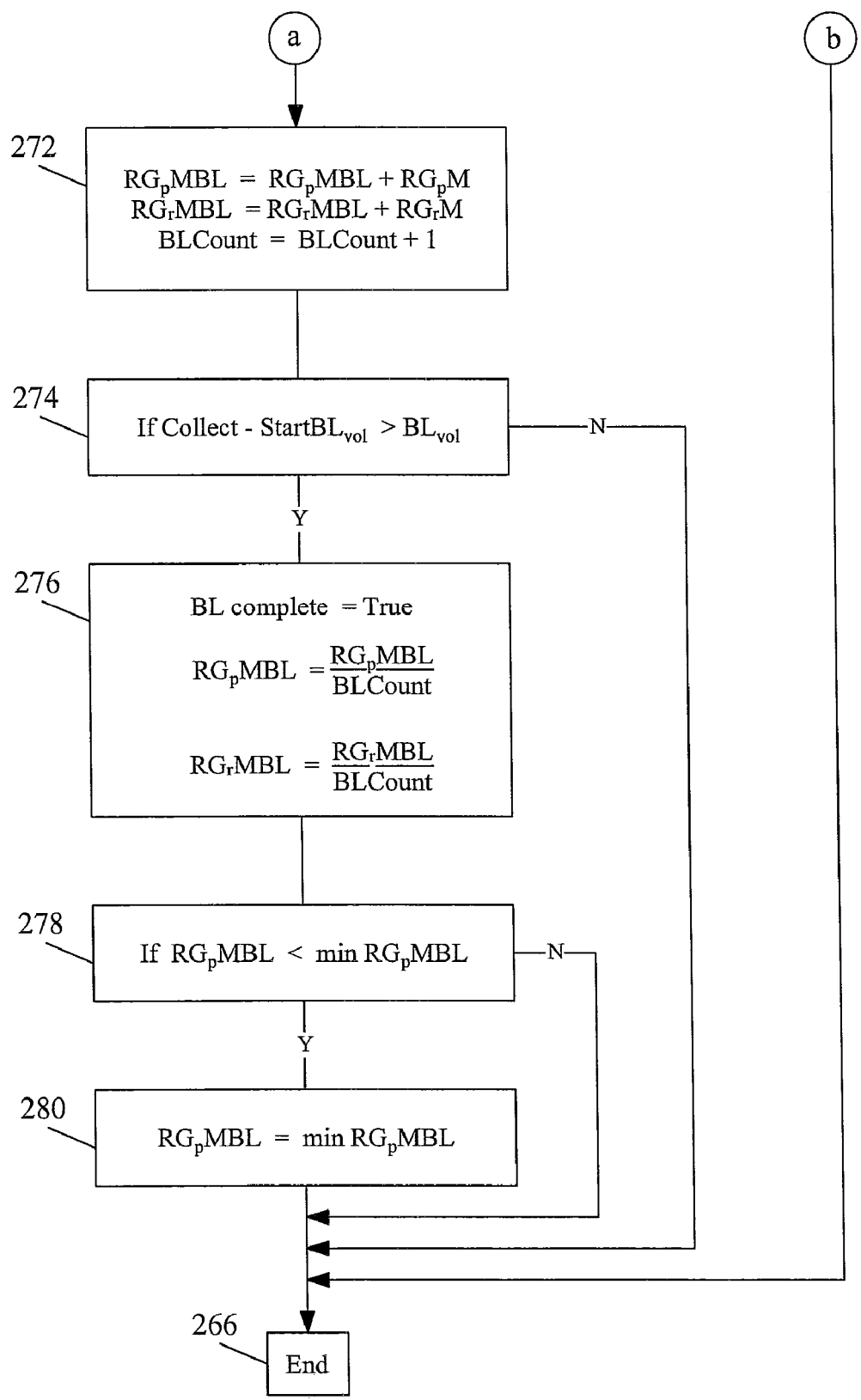

Calculation of the thresholds depends on detecting baseline conditions, as illustrated in the flow chart of baseline subroutine 262 of FIG. 13. During the initial stages of a donation procedure, the device 6 will periodically check for conditions for establishing baseline conditions for the output of the red-green sensor 116, that is, to calibrate the sensor to the particular donor. The controller 158 checks 264 if a baseline has not been established, if the procedure has completed priming so that blood components are flowing through the sensor 116, and if at least plasma is detected. If the initial checks fail, the subroutine terminates 266, to be re-tried at a later time. If the initial checks are met, the subroutine tests 268 for conditions favorable for establishing the baseline. The tests may include checks for stable flow conditions, as listed at qualification step 268 in FIG. 13. Variable Cr is platelet concentration, based on the output of a red light sensor in the red-green sensor 116. Cr should be greater than a pre-selected constant, CrBaselineMin, indicating that platelet flow in the line 112 is being detected. The average rate of change of platelet concentration, CrSlopeAve, should fall within a range bounded by a minimum negative or falling rate of change, SlopeMin, and a maximum positive or raising rate of change, SlopeMax. These conditions indicate that the platelet concentration is sufficiently close to a constant value that baseline values can be measured. Also, the amount of fluid collected since a significant disturbance in flow ("Collect-Vol (dist)") should be greater than a pre-determined volume, thus indicating that steady-state conditions of flow have been established. The state or phase of the process being controlled by the controller should not be trying to either flush the separation chamber or flush platelets or flush white blood cells out of the chamber 134. The median red-green ratio, RGrMd, that is, a statistical median of the ratio of the red light sensor to the green light sensor over a selected time should be less than a selected constant BLmax. In addition, the rate of change of the median red-green ratio, "RGrMdSlope", should also fall within a range bounded by a minimum negative or falling rate of change, "BLSlopeMin", and a maximum positive or rising rate of change, "BLSlopeMax". This further indicates stable flow conditions consistent with accurate baseline measurement. Finally, both a median red-green peak-to-peak ratio, "RGpMd", and a rate of change of the median of the red-green peak-to-peak ratio, "RGpMdSlope", should fall within predetermined maximum and minimum limits, as shown in qualification step 268.

If the foregoing conditions are not met, a baseline cannot be established. An alternative collection mechanism is implemented at step 270 by clearing flags for a baseline count, a red-green peak-to-peak count, and a median red-green ration count, and by starting a control sequence based on a baseline volume.

If a condition of flow stability is detected (step 268), a series of measurements are taken 272. For example, the strength of the red light sensor signal is compared to the strength of the green light sensor signal. The median value of this ratio over a measurement period is added to a cumulative value "RGrMBL". At the same time the difference between the peak red light sensor signal and the peak green light sensor signal is added to another cumulative value "RGpMBL". Each time a new measurement is taken a counter "BLCount" is incremented. When a complete series of measurements has been taken, either after a selected volume of fluid has passed the sensor (step 274) or as flow becomes unstable, the two cumulative values are divided by the counter to calculate 276 average baseline values for the red-green ratio and for the red-green peak-to-peak value. In addition, a flag indicating that baseline values have been calculated is set to "true". Finally, if the measured and calculated peak-to-peak value is less than a pre-determined minimum 278, the baseline red-green peak-to-peak value is set to the predetermined minimum 280.

If baseline values can be established as described above, the device is able to fill the separation chamber 134 with white blood cells and empty the cells into a collection bag efficiently, thereby improving the donation process. As will be described in connection with FIG. 14, detecting either a red-green ratio higher than the red-green ratio baseline value or a peak-to-peak value higher than the peak-to-peak baseline value will cause the device to flush the chamber 134. In addition, the chamber empties if there has been excessive flow volume without a trigger event. An apparent baseline trigger event is ignored as an error if there has been too little fluid flow through the chamber 134.

Figure 14:
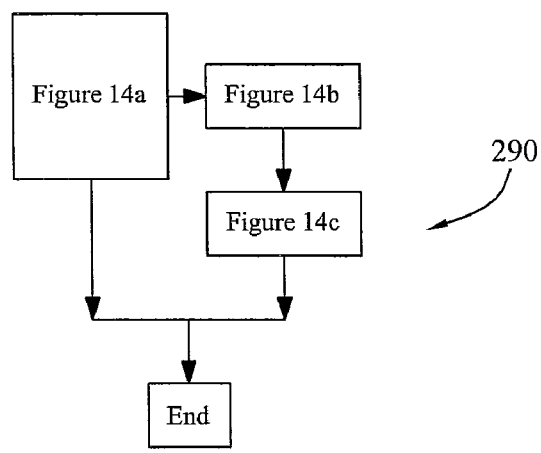
FIG. 14 is a flow chart of an algorithm for implementing a cell separation chamber trigger for collection of blood cells.
Figure 14A:
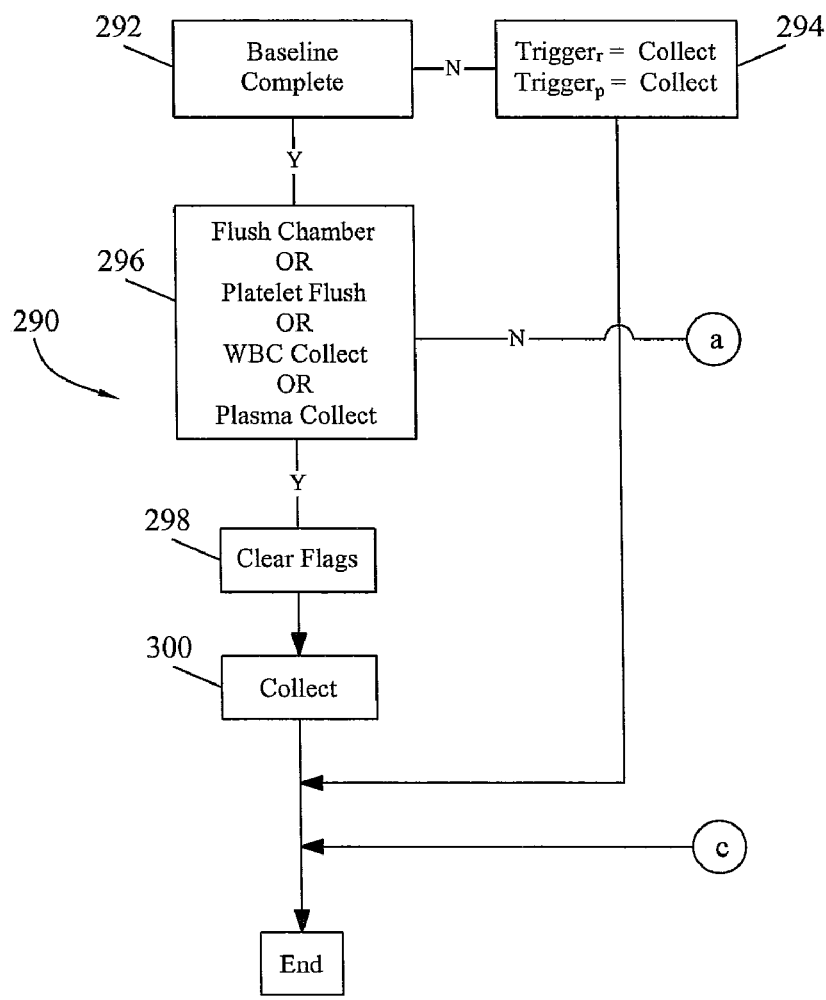
Figure 14B:
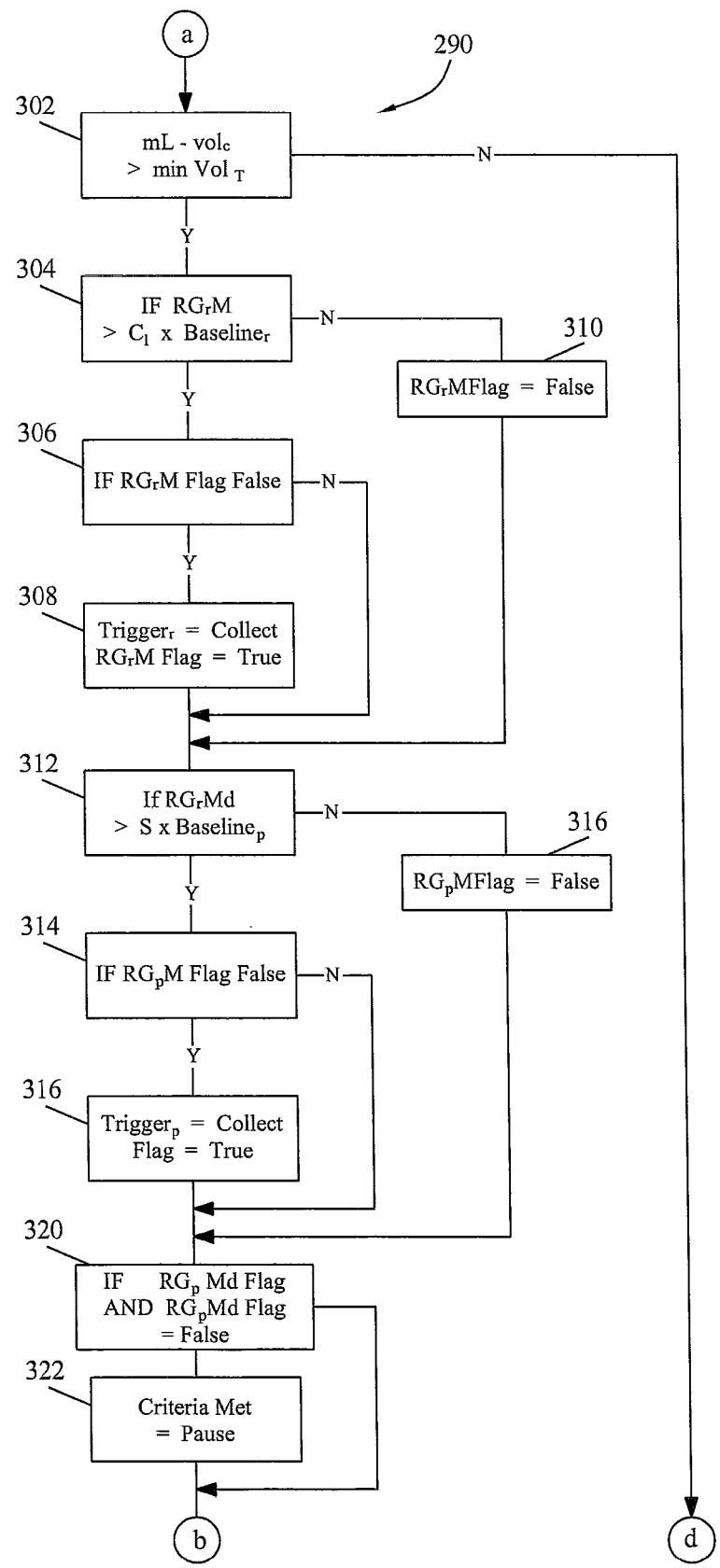
Figure 14C:
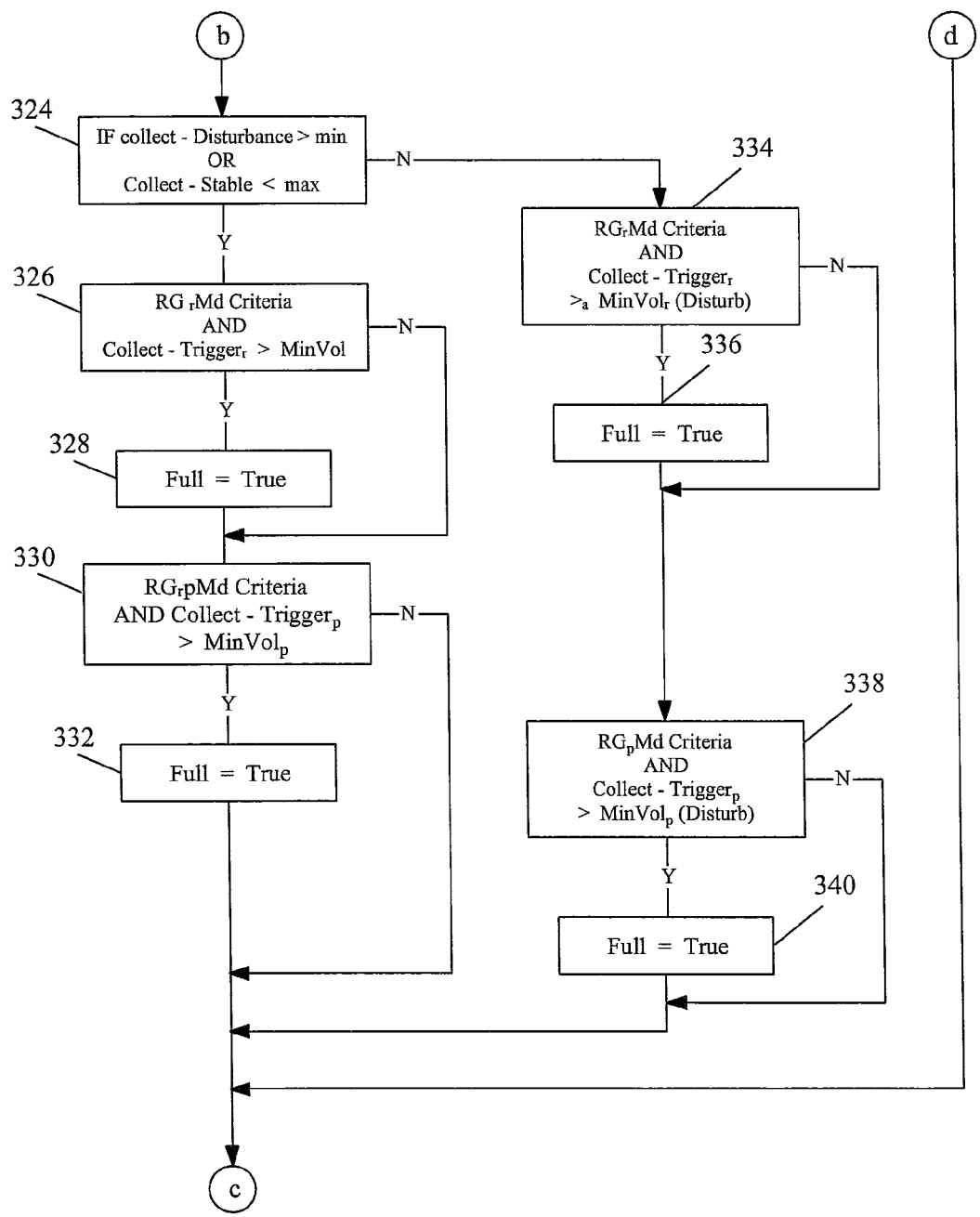

A white blood cell collection algorithm 290, shown in FIG. 14, begins by testing 292 for the completion of the baseline algorithm 262. If baselines have not been established, triggers associated with the red-green ratio and with the peak-to-peak are set 294 to a pre-selected constant value. Otherwise, the algorithm 290 checks 296 for any device-controlled special flow conditions, that is, if the device is attempting to flush the chamber 134, or to empty platelets out of the chamber, or to collect plasma, or to collect white blood cells. If none of these conditions are detected, the algorithm can monitor for a triggering event, as described below. If any of these conditions are present, the chamber is in the process of being emptied. Flags are set 298 to indicate that a new collection cycle will be started, and blood components in the chamber 134 are collected 300. Depending on the nature of the blood components, the contents of the chamber 134 may be returned to the donor, or collected in collection bags. As is known in the art, valves on the device 6 direct fluid in an appropriate path in response to pump-driven increased fluid flow rates.

Next, the algorithm tests 302 for certain limits. If the amount of fluid passing through the chamber 134 since the last time the chamber was emptied ("mL-volc") is greater than a minimum fill volume, the algorithm can test for the red-green or peak-to-peak criteria. The minimum fill volume may be predetermined constant or, preferably, may be determined by detecting particle flow into the chamber 134 with the camera, calculating the flow volume necessary to fill the chamber with particles, and setting the minimum fill volume to a portion, for example one half, of that calculated volume. This latter fill volume is donor specific and automatically determined by the device 6. If the sensed red-green ratio exceeds 304 the product of the red-green baseline (as determined above) and a constant, and if a re-green ratio flag is false 306, the red-green trigger is set 308 to "collect", thereby initiating a white blood cell collection, and the red-green flag is set to "true", thereby indicating that a collection process has been started in a particular collection cycle. If the sensed red-green ration does not exceed 304 the above-mentioned product, the red-green flag is set 310 to false, and the algorithm begins to test the peak-to-peak criteria.

If the sensed peak-to-peak measurement exceeds 312 the product of the peak-to-peak baseline (as determined above) and a constant, and if a peak-to-peak flag is false 314, the peak-to-peak trigger is set 316 to "collect", thereby initiating a white blood cell collection, and the peak-to-peak flag is set to "true", thereby indicating that a collection process has been started in a particular collection cycle. If the sensed peak-to-peak measurement does not exceed 312 the above-mentioned product, the peak-to-peak flag is set 318 to false.

If both the red-green flag and the peak-to-peak flag are false 320, a "chamber full" flag is set to false 322, indicating to other parts of the system that flow conditions, valve settings and pump speeds should be maintained while collection of white blood cells in the chamber 134 continues.

The red-green ratio and peak-to-peak criteria are sensitive indicators that the chamber 134 has filled with white blood cells, thus allowing an efficient collection procedure. Flow conditions, however, may continue to be relatively stable or there may be variations or "disturbances" in the flow. Such disturbances may be related to the particular donor's blood characteristics or may be related to the general environment, including conditions of the device 6 or the room where the donation is being given. The algorithm distinguishes, therefore, between such conditions and applies sensitive criteria when flow conditions are smooth and less sensitive criteria when flow disturbances are detected. If the flow is stable, sensitive criteria should be used to detect a trigger event, that is, a condition indicating that the chamber 134 has collected sufficient white blood cells and should be emptied. If the flow is unstable, less sensitive criteria should be used. At step 324, if either a collection volume minus a volume to a flow disturbance is greater than a minimum volume (implying that the flow is stable) or the collection volume minus a stable flow volume is less than a maximum stable flow volume (implying that a significant period has elapsed without a triggering event), sensitive criteria used. If the red-green criteria has been met and the collect volume minus a red-green trigger volume is greater than a pre-selected minimum red-green trigger volume 326, the "chamber full" flag is set to true 328, indicating to other parts of the system that flow conditions, valve settings and pump speeds should be changed to flush white blood cells from the chamber 134 into a collection bag. Similarly, if the peak-to-peak criteria has been met and the collect volume minus a peak-to-peak trigger volume is greater than a pre-selected minimum peak-to-peak trigger volume 330, the "chamber full" flag is set to true 332, again indicating to other parts of the system that flow conditions, valve settings and pump speeds should be changed to flush white blood cells from the chamber 134 into a collection bag.

On the other hand, at step 324, if neither a collection volume minus a volume to a flow disturbance is greater than a minimum volume nor the collection volume minus a stable flow volume is less than a maximum stable flow volume, less sensitive criteria used. If the red-green criteria has been met and the collect volume minus the red-green trigger volume is greater 334 than a pre-selected minimum red-green trigger volume for disturbed flow (greater than the minimum red-green trigger volume of step 326), the "chamber full" flag is set to true 336, indicating to other parts of the system that flow conditions, valve settings and pump speeds should be changed to flush white blood cells from the chamber 134 into a collection bag. Similarly, if the peak-to-peak criteria has been met and the collect volume minus a peak-to-peak trigger volume is greater 338 than a pre-selected minimum peak-to-peak trigger volume for disturbed flow (greater than the minimum peak-to-peak trigger volume of step 330), the "chamber full" flag is set to true 340, again indicating to other parts of the system that flow conditions, valve settings and pump speeds should be changed to flush white blood cells from the chamber 134 into a collection bag.

The present invention allows for efficient collection of white blood cells from a single donor by monitoring the outflow characteristics of the cell collection chamber 134. Such efficient collection is believed to contribute to reduced donation times and higher quality white cell collections.

Although the inventive device and method have been described in terms of collecting white blood cells, this description is not to be construed as a limitation on the scope of the invention. The invention may be practiced to collect other components by appropriate selection of the red-green ratio or peak-to-peak measurements to relate to the component being collected in the chamber 134. It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A blood cell collection system comprising
   a centrifuge rotor;
   a blood processing chamber mounted on said rotor;
   a flushable cell separation chamber in fluid communication with said processing chamber;
   a detector coupled to an outflow line of said cell separation chamber, said detector sensing optical characteristics of fluid in said outflow line;
   a controller receiving a signal from said detector and discriminating between types of fluid in said outflow line, and said controller causing collected cells in said cell separation chamber to be emptied in response to the type of fluid in said outflow line;
   at least one pump controlled by said controller and operable to increase fluid flow through said cell separation chamber, whereby said collected cells are emptied from said cell separation chamber.

2. The blood cell collection system of claim 1 wherein said detector detects green and red intensities.

3. The blood cell collection system of claim 2 wherein said intensity is computed as the ratio of red intensity to green intensity during a first predetermined length of time.

4. The blood cell collection system of claim 2 wherein said intensity is computed as peak red light intensity-to-peak green light intensity during a second predetermined length of time.

5. The blood cell collection system of claim 1 wherein a flow of a first type of fluid is established as a baseline condition and a change to said first type of fluid is detected when a change in optical characteristics is detected, said change being a function of said baseline condition.

6. The blood cell collection system of claim 5 wherein said baseline condition is established when said flow of said first type of fluid has reached a stable state.

7. The blood cell collection system of claim 6 wherein said stable state is recognized when a rate of change of the intensity of said optical characteristic is within a pre-determined range.

8. The blood cell collection system of claim 6 wherein said stable state is recognized when a ratio of red intensity to green intensity is within a pre-determined range.

9. The blood cell collection system of claim 6 wherein said stable state is recognized when a peak red light intensity to a peak green light intensity is within a pre-determined range.

10. The blood cell collection system of claim 1 wherein a bolus of said fluid in said cell separation chamber is delivered to a collection container by increasing flow rate and diverting the output of said cell separation chamber into said collection container.

11. The blood cell collection system of claim 10 wherein said apparatus passes a fluid into said cell separation chamber to flush white blood cells.

12. The blood cell collection system of claim 1 further comprising an optical sensor coupled to an inflow line into said cell separation chamber, said optical sensor detecting characteristics of fluid flowing into said cell separation chamber.

13. The blood cell collection system of claim 12 further comprising means for calculating a volume of cells collected in said cell separation chamber based on said characteristics of fluid flowing into said chamber and flushing said cell separation chamber when a predetermined volume of cells is collected.

14. The blood cell collection system of claim 1 comprising means for calculating a volume of cells collected in said cell separation chamber based on system parameters and flushing said cell separation chamber when a predetermined volume of cells is collected.

15. The blood cell collection system of claim 1 comprising means for calculating a volume of cells collected in said cell separation chamber based on patient characteristics and flushing said cell separation chamber when a predetermined volume of cells is collected.

16. The blood cell collection system of claim 15 wherein said cell separation chamber is flushed in response to said type of fluid in said outflow line only if said calculated volume of cells is greater than a predetermined amount.

17. The blood cell collection system of claim 15 wherein said cell separation chamber is flushed if said calculated volume of cells is greater than a second predetermined amount even if a change in fluid type in said outflow line has not been detected.

18. A method for collecting blood cells comprising
providing a blood cell collection system having a flushable cell separation chamber
detecting optical characteristics of fluid in an outflow line of said cell separation chamber;
discriminating between types of fluid in said outflow line; and
causing collected cells in said cell separation chamber to be emptied in response to the type of fluid in said outflow line.

19. The method of claim 18 wherein said detecting step detects green and red intensities.

20. The method of claim 19 wherein said intensity is computed as the ratio of red intensity to green intensity during a first pre-determined length of time.

21. The method of claim 19 wherein said intensity is computed as peak red light intensity-to-peak green light intensity during a second pre-determined length of time.

22. The method of claim 18 further comprising
establishing a baseline condition and detecting a change to said first type of fluid when a change in optical characteristics is detected, said change being a function of said baseline condition.

23. The method of claim 22 wherein said baseline condition is established when said flow of said first type of fluid has reached a stable state.

24. The method of claim 23 wherein said stable state is recognized when a rate of change of the intensity of said optical characteristic is within a pre-determined range.

25. The method of claim 23 wherein said stable state is recognized when a ratio of red intensity to green intensity is within a pre-determined range.

26. The method of claim 23 wherein said stable state is recognized when a peak red light intensity to a peak green light intensity is within a pre-determined range.

27. The method of claim 18 wherein a bolus of said fluid in said cell separation chamber is delivered to a collection container by increasing flow rate and diverting the output of said cell separation chamber into said collection container.

28. The method of claim 18 further comprising detecting characteristics of fluid flowing into said cell separation chamber.

29. The method of claim 18 comprising calculating a volume of cells collected in said cell separation chamber based on system parameters and flushing said cell separation chamber when a predetermined volume of cells is collected.

30. The method of claim 18 comprising calculating a volume of cells collected in said cell separation chamber based on patient characteristics and flushing said cell separation chamber when a predetermined volume of cells is collected.

31. The method of claim 30 wherein said cell separation chamber is flushed in response to said type of fluid in said outflow line only if said calculated volume of cells is greater than a predetermined amount.

32. The method of claim 30 wherein said cell separation chamber is flushed if said calculated volume of cells is greater than a second predetermined amount even if a change in fluid type in said outflow line has not been detected.

* * * * *